United States Patent [19]

Bieniarz et al.

[11] Patent Number: 5,789,219
[45] Date of Patent: Aug. 4, 1998

[54] PHOSPHATASE ACTIVATED CROSSLINKING CONJUGATING AND REDUCING AGENTS; METHODS OF USING SUCH AGENTS; AND REAGENTS COMPRISING PHOSPHATASE ACTIVATED CROSSLINKING AND CONJUGATING AGENTS

[75] Inventors: Christopher Bieniarz, Highland Park; Douglas F. Young, Grayslake; Michael J. Cornwell, Morton Grove; Mazhar Husain, Libertyville; Zbigniew Skrzypczynski, Vernon Hills, all of Ill.

[73] Assignee: Abbott Laboratories, Abbott Park, Ill.

[21] Appl. No.: 655,067

[22] Filed: May 29, 1996

Related U.S. Application Data

[62] Division of Ser. No. 349,167, Dec. 2, 1994.

[51] Int. Cl.$^6$ .............. C12N 11/14; C12N 11/06; C12N 11/08; C07K 17/06
[52] U.S. Cl. .............. 435/188; 435/174; 435/176; 435/181; 436/500; 436/518; 436/532; 530/391.1; 530/391.5; 530/811; 530/816
[58] Field of Search ............... 530/391.1, 391.5, 530/811, 816; 435/174, 176, 181, 188; 436/500, 518, 532

[56] References Cited

U.S. PATENT DOCUMENTS

| | | |
|---|---|---|
| 3,969,287 | 7/1976 | Jaworek et al. |
| 4,166,105 | 8/1979 | Hirschfeld et al. |
| 4,169,137 | 9/1979 | Hirschfeld et al. |
| 4,520,110 | 5/1985 | Stryer et al. |
| 4,542,104 | 9/1985 | Stryer et al. |
| 4,657,853 | 4/1987 | Freytag et al. |
| 4,843,126 | 6/1989 | Quinn ........................ 525/162 |
| 4,970,074 | 11/1990 | Fiechtner et al. |
| 4,994,385 | 2/1991 | Bieniarz et al. |
| 5,053,520 | 10/1991 | Bieniarz et al. |
| 5,191,066 | 3/1993 | Bieniarz et al. |
| 5,376,403 | 12/1994 | Capote et al. ................ 427/96 |

FOREIGN PATENT DOCUMENTS

| | | |
|---|---|---|
| 0049475A2 | 4/1982 | European Pat. Off. |
| 0175560 | 3/1986 | European Pat. Off. |
| 0506431A1 | 9/1992 | European Pat. Off. |
| 0 562 624 A2 | 9/1993 | European Pat. Off. |
| WO91/08287 | 6/1991 | WIPO. |
| WO 92/08790 | 5/1992 | WIPO. |
| 9502422 | 1/1995 | WIPO. |
| 9531434 | 11/1995 | WIPO. |

OTHER PUBLICATIONS

B. Connolly et al., *The Journal of Biological Chemistry*, 267 (7): 3382–3384 (1982).

Bioconjugate Chem. C. Bieniarz, et al., *Thiolate and Phosphorothioate Functionalized Fluoresceins and Their Use as Fluorescent Labels*, vol. 5, pp. 31–39, 1994.

Tetrahedron Letters, C. Bieniarz, et al, *A Facile, High-Yielding Method for the Conversion of Halides to Mercaptans*, vol. 34, No. 6, pp. 939–942, 1993.

Enzyme Microb. Technol., S.S. Wong, et al., *Chemical crosslinking and the stabilization of proteins and enzymes*, vol. 14, pp. 866–874, 1992.

J. Am. Chem. Soc., N. L. St.Clair, et al, *Cross–linked Enzyme Crystals as Robust Biocatalysts*, vol. 114, No. 18, pp. 7314–7316, 1992.

Bioorganic Chemistry, J. Suh, et al, *Enhancement of Durability of Chymotrypsin through Cross–Linking with Poly (allylamine)*, vol. 20, pp. 223–235, 1992.

Tetrahedron Letters, P. Wang, et al., *The Catalytic Formation of Peptide Bonds with Carbohydrate Protein Conjugates of Proteases [CPC (Proteases)]* vol. 32, No. 47, pp. 6827–6830, 1991.

Tetrahedron Letters, T.G. Hill et al., *Carbohydrate Protein Conjugates (CPC): The Design of New Materials to Stabilize Enzymes*, vol. 32, No. 47, pp. 6823–6826, 1991.

Boehringer Mannheim Catalogue, 1991.

TIBTECH, E.Y. Shami, et al, *Stabilization of biologically active proteins*, vol. 7, pp. 186–190, Jul., 1989.

(List continued on next page.)

*Primary Examiner*—Mary E. Ceperley
*Attorney, Agent, or Firm*—John F. Levis; Regina M. Anderson

[57] ABSTRACT

The present invention provides crosslinking, conjugating and reducing agents which are functional with at least one phosphorothioate monoester group ($-SPO_3^{-2}$). Crosslinking and conjugation methods as well as solid phase reagents and conjugates which are useful in immunoassays are also provided.

Crosslinking and conjugating agents of the invention generally comprise a compound corresponding to the formula (I), shown below, wherein n at least 1 and Q is a straight or branched monomer, polymer or oligomer having an average molecular weight between about 200 and about 1,000,000. Additionally, when n is 1, Q comprises at least 1 additional reactive functionality.

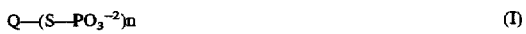

$$Q-(S-PO_3^{-2})_n \quad (I)$$

The reducing agents that are provided conform to a compound of the formula (Y), shown below, wherein (A) and (Z) can be independently selected from $C_1-C_5$ alkyl and CONH $(CH_2)_p$ wherein p is an integer between 1 and 5.

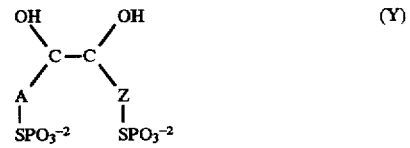

10 Claims, 18 Drawing Sheets

OTHER PUBLICATIONS

TIBS, Glazer, A.N., et al, *Phycofluor probes*, pp. 423–427, 1984.

J. Am. Chem. Soc., A. Pellack et al. *Enzyme Immobilization by Condensation Copolymerization into Cross-Linked Polyacrylamide Gels*[1,] vol. 102, pp. 6324–6336,1980.

Alexander Hampton, et al. "Analogs of Inosine 5'-Phosphate with Phosphorus-Nitrogen and Phosphorus-Sulfur Bonds. Binding and Kinetic Studies with Inosine 5'-Phosphate Dehydrogenase", *Biochemistry*, vol. 8, No. 6 (1969), pp. 2303–2311.

John C. Livesey, et al. "Binding of Aminoalkylphosphorothioate Radioprotective Drugs to Rodent Tissue Proteins", *Biochemical Pharmacology*, vol. 39, No. 11 (1990), pp.1807–1812.

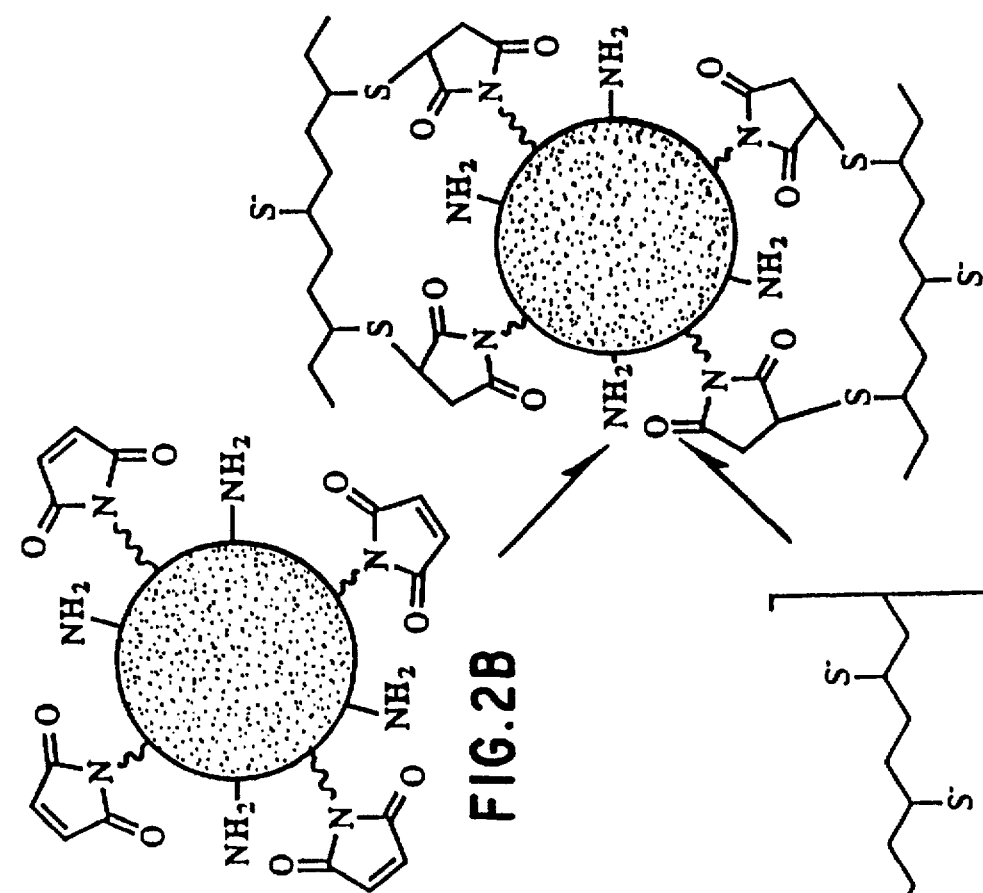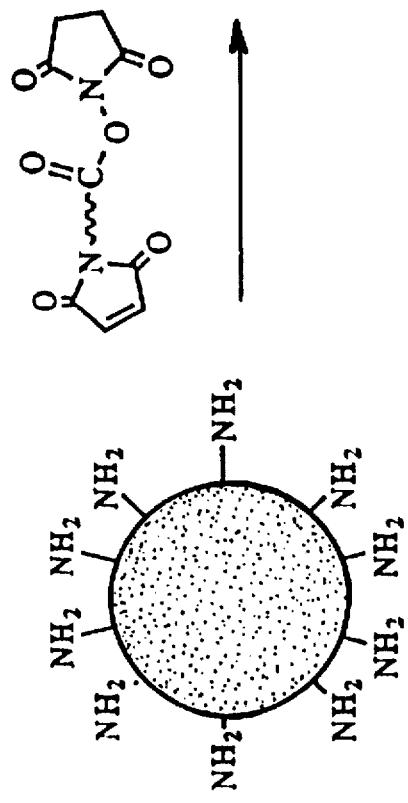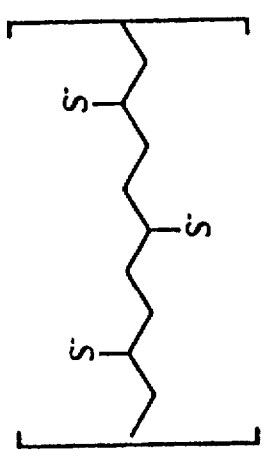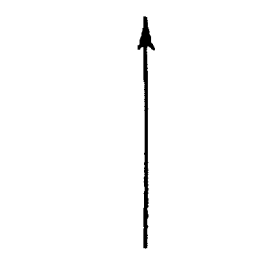

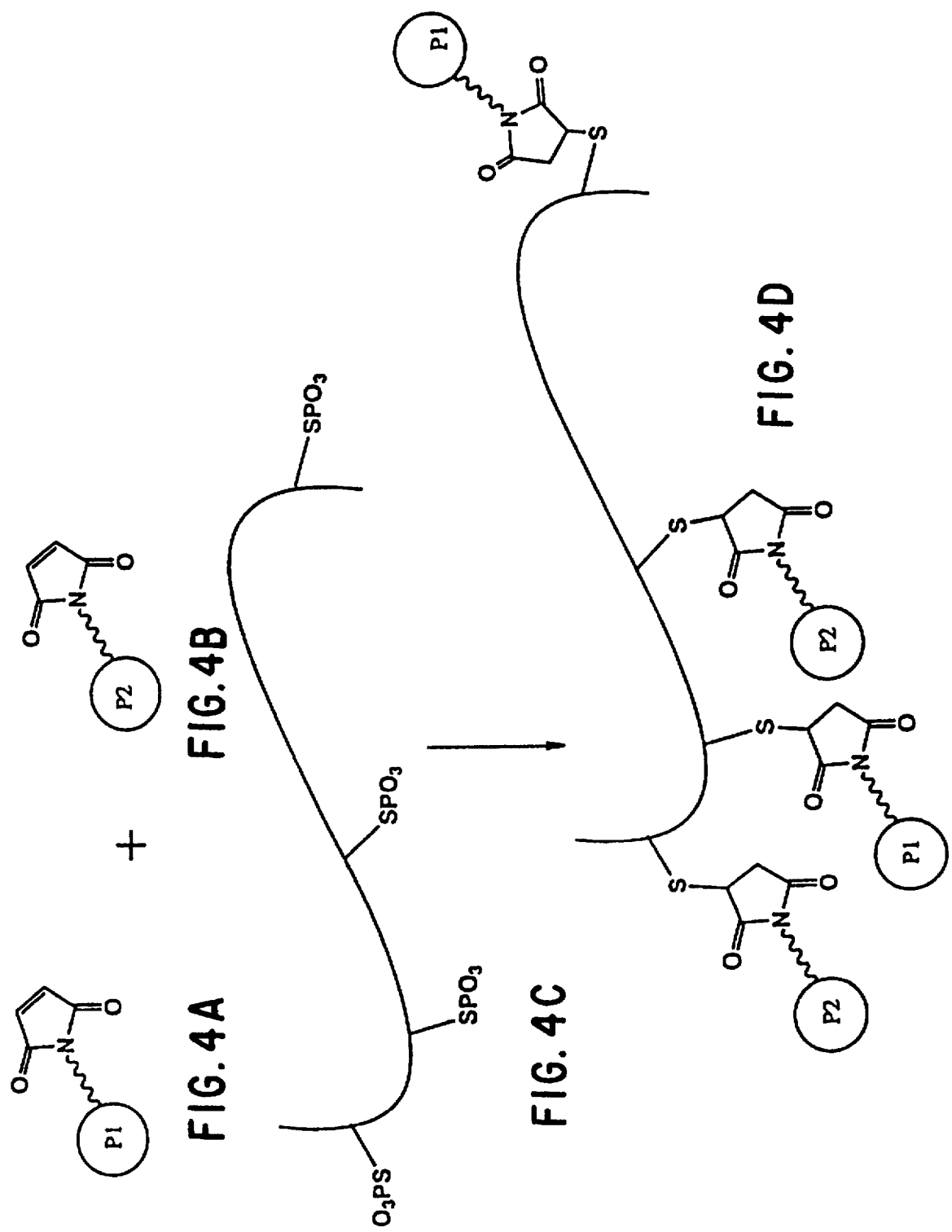

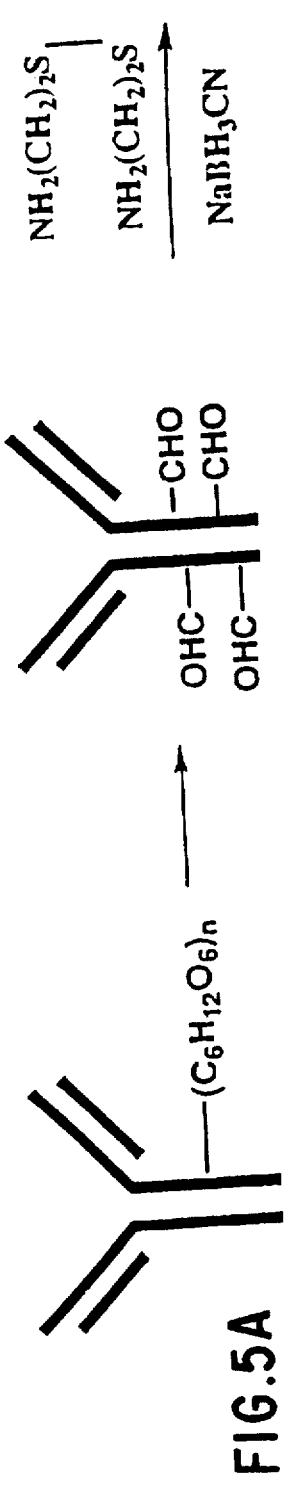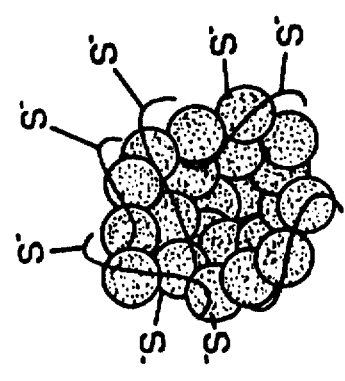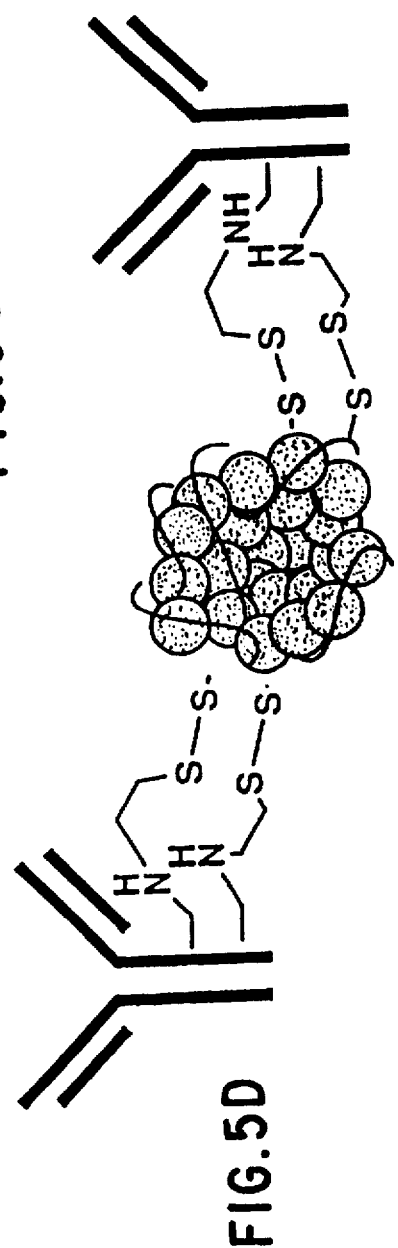
FIG.5A  FIG.5B  FIG.5C  FIG.5D

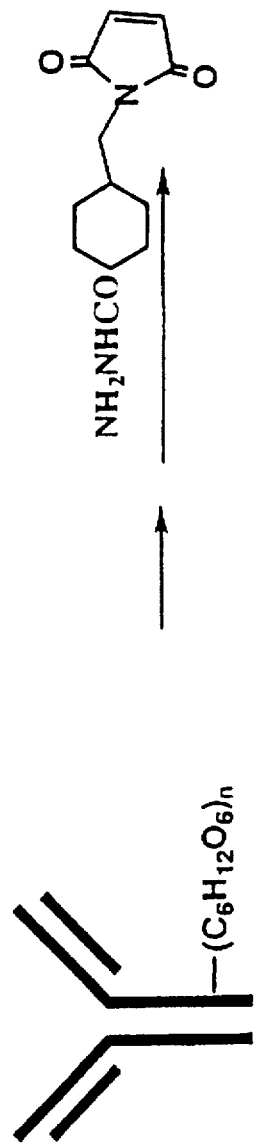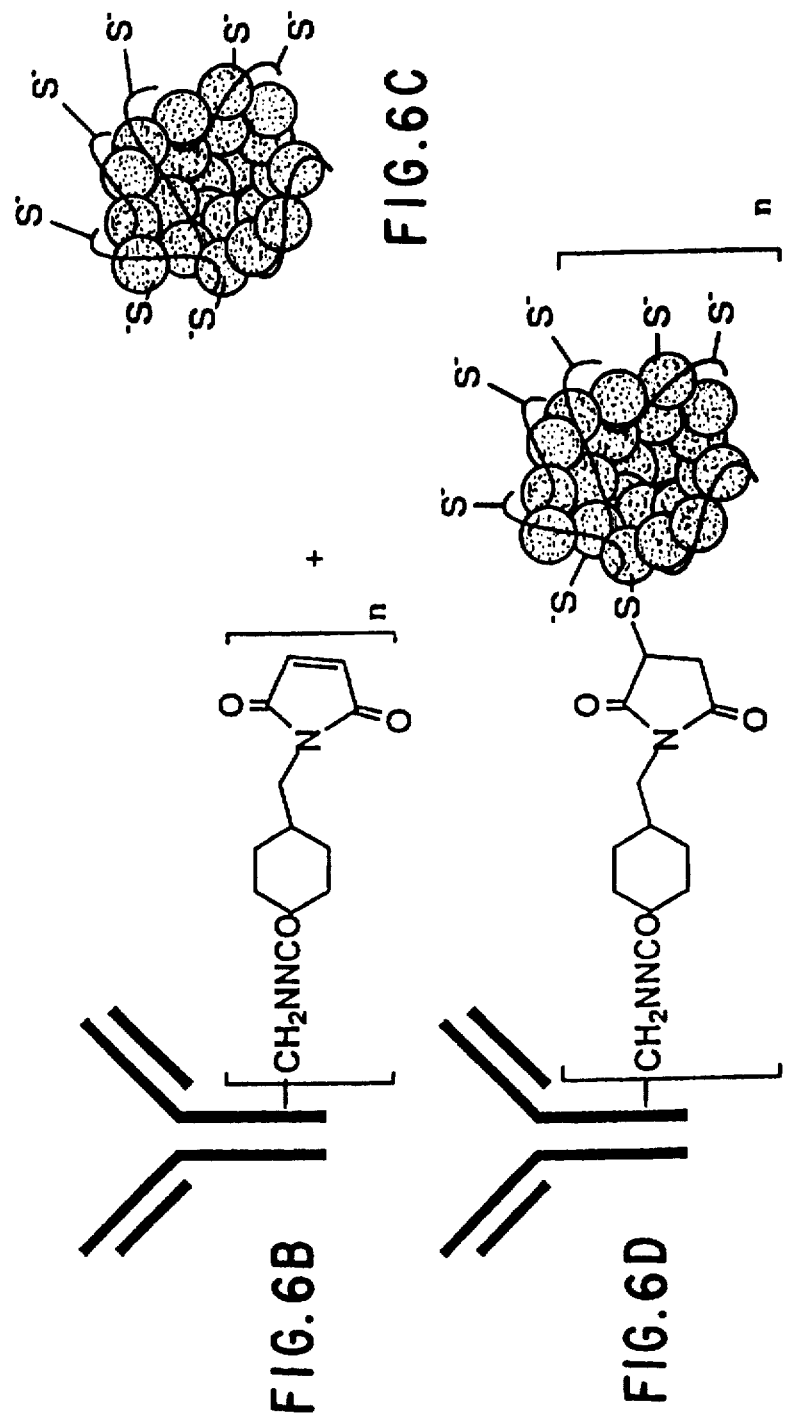
FIG.6A
FIG.6B
FIG.6C
FIG.6D

PHOSPHATASE ACTIVATED CROSSLINKING CONJUGATING AND REDUCING AGENTS; METHODS OF USING SUCH AGENTS; AND REAGENTS COMPRISING PHOSPHATASE ACTIVATED CROSSLINKING AND CONJUGATING AGENTS

This is a divisional of copending applications Ser. No. 08/349,167 filed on Dec. 2, 1994.

FIELD OF THE INVENTION

The present invention relates to crosslinking, conjugating and reducing agents and, in particular, relates to phosphorothioate monoester functional crosslinking, conjugating and reducing agents.

BACKGROUND OF THE INVENTION

Immunoassays have become a useful diagnostic tool for detecting the presence or amount of an analyte in a test sample. Various forms of immunoassays, as well as the reagents and procedures necessary to perform such assays, are well known in the art.

One form of a conventional solid-phase immunoassay is a "sandwich assay" which involves contacting a test sample suspected of containing an analyte with a substantially solid inert plastic, latex or glass bead or microparticle, or other support material which has been coated with a protein or another substance capable of binding the analyte to the surface of the support. The analyte and the protein or substance capable of binding the analyte are commonly referred to as a "binding pair" or individually known as "binding members", and a support material coated with a binding member is variably referred to as a "solid phase reagent". After the analyte is bound to the support material the remaining test sample is removed from the support and the analyte bound support material is treated with a second binding member. The second binding member can be conjugated to a signal generating group such as an enzyme, a fluorophore or a chemiluminescent label and collectively, the binding member/signal generating group complex is variably referred to as a "conjugate" or "indicator reagent". The conjugate becomes bound to the analyte which is bound on the support and the solid support, having the first binding member, the analyte and conjugate bound thereon is separated from any unbound conjugate, typically with one or more wash steps. In the case of an enzyme immunoassay, an indicator substance, for example, a chromogenic substrate, is added which reacts with the enzyme to produce a color change. The color change can be observed visually, or more preferably by an instrument, to indicate the presence or amount of an analyte in the test sample. For solid phase fluorescence or chemiluminescence immunoassays, fluorescent labeled binding members can be monitored using excitation at an appropriate wavelength, while chemiluminescent labeled binding members can be monitored after a reaction which chemically activates the chemiluminescent label and generates light which can be detected by photometric means.

Immunoassay reagents such as a solid phase reagent or a conjugate are typically manufactured in bulk and small amounts of the bulk reagents are used to perform individual assays. Remaining bulk reagents are then stored for subsequent assays. The stability of these reagents is paramount to providing analytical methods which exhibit precision and uniformity among individual assays. Instability of such reagents provides for unreproducible assay results as well as an increase in the costs of medical services because unstable bulk reagents must be discarded.

Various methods have been used to increase the stability of immunoassay reagents by preserving the integrity and/or activity of the compounds that comprise the reagents. Some methods of preserving immunoassay reagents involve placing additives such as proteins or carbohydrates into solutions that contain the reagents. Another method of preserving assay reagents includes adding reducing agents (variously referred to as "anti-oxidants") to lyophilized assay reagents. Unfortunately, over time, reducing agents are themselves oxidized and consequently provide only short term reagent protection. Chemical crosslinking has also become accepted as a method for stabilizing macromolecules and thereby preserving their integrity and activity.

Chemical crosslinking can effectively be accomplished by intermolecular crosslinking or intramolecular crosslinking wherein molecules having a greater degree of crosslinking are generally more stable than molecules having a lesser degree of crosslinking. Intramolecular crosslinking refers to covalent bonds or crosslinks that are formed within a single multimeric or monomeric chemical entity. Hence, disulphide bonds occurring within an antibody are exemplary of intramolecular crosslinking. On the other hand, intermolecular crosslinking refers to covalent bonds or crosslinks that are formed between more than one distinct chemical entity such as the bonds which are formed when one compound is conjugated to another. Accordingly, an immunoassay's indicator reagent comprising, for example, an antibody attached or conjugated to an enzyme, is exemplary of intermolecular crosslinking. Additionally, an immunoassay's solid phase reagent or an affinity chromatography gel comprising an antibody bound to a chromatographic gel are further examples of intermolecular crosslinking. While intermolecular crosslinking, as exemplified above, is an effective means of conjugating one chemical entity to another, generally, the degree of crosslinking is minimal and the stability of compounds conjugated in this manner is seldom enhanced.

Crosslinking a chemical entity through multipoint intermolecular crosslinking, however, can greatly enhance the compound's stability. Multipoint intermolecular crosslinking typically results in the formation of a plurality of bonds between a crosslinking agent and the compound which is crosslinked. Such crosslinking is most commonly associated with the bonds formed between a soluble entity such as, for example, a polymer and a protein such as, for example, an enzyme.

Examples of intramolecular and intermolecular crosslinking have previously been described. For example, Wong et al., *Enzyme Microb. Technol.*, vol 14, pg 866–874 (1992); generally outlines techniques and reagents for intramolecularly and intermolecularly crosslinking compounds. Additionally, U.S. Pat. No. 4,652,524 and U.S. Pat. No. 4,657,853 disclose the crosslinking of multiple enzymes to a polymer, and further crosslinking the polymeric enzyme to a binding member. European Patent Application No. 0 049 475 discloses a method for multipoint intermolecular crosslinking an enzyme with a soluble polymer. Unfortunately, however, the aforementioned methods require harsh conditions to effect crosslinking, lack control over the crosslinking process, and/or result in randomly polymerized protein aggregates which are often non-soluble. Moreover the biological performance of the crosslinked entity is often negatively affected as manifested by, for example, lower binding affinities, diminished enzymatic turnover, recognition impairment by specific ligands, and the like.

SUMMARY OF THE INVENTION

The present invention provides crosslinking, conjugating and reducing agents which are functional with at least one phosphorothioate monoester group ($—SPO_3^{-2}$). Agents of the invention can be activated by deprotecting or hydrolyzing the phosphate group(s) comprising the phosphorothioate monoester(s). Upon activation, the agents herein provided display an nucleophilic thiol group which can be used in crosslinking, reducing and/or conjugating capacities. The crosslinking, conjugating and reducing agents herein provided can, for example, be activated in a suitable pH environment but the phosphate group(s) can also be hydrolyzed with a phosphate hydrolyzing enzyme. Advantageously, through enzymatic activation, innocuous phosphate ions and activated agent are the major activation reaction products.

Crosslinking and conjugating agents of the invention generally comprise a compound corresponding to the formula (I), shown below, wherein n is at least 1 and Q is a straight or branched monomer, polymer or oligomer having an average molecular weight between about 200 and about 1,000,000. Additionally, when n is 1, Q comprises at least 1 additional reactive functionality.

A method for crosslinking and conjugating compounds which is provided herein comprises activating a compound corresponding to the formula (I) to form an activated agent and contacting the activated agent with at least one compound which is functional with an electrophilic group. Preferably, the compound of the formula (I) is activated with a pH of between about 4.0 and about 5.5 or with a phosphatase enzyme.

Conjugates and solid phase reagents are also provided herein. A conjugate as taught herein will generally comprise at least one binding member and at least one detectable moiety bound to the residue of a compound corresponding to the formula (I). On the other hand, a solid phase reagent will generally comprise at least one binding member and a solid phase attached to the residue of a compound having the formula (I).

Reducing agents are also provided which generally conform to a compound of the formula (Y), shown below, wherein (A) and (Z) can be independently selected from $C_1-C_5$ alkyl and $CONH(CH_2)_p$ wherein p is an integer between 1 and 5.

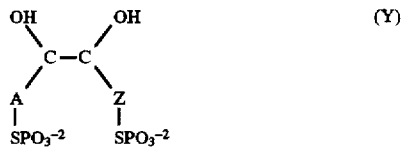

BRIEF DESCRIPTION OF THE DRAWINGS

FIG. 2(a)–(e) illustrate a method of stabilizing a compound.

FIG. 4(a)–(d) illustrate a method of conjugating two distinct chemical entities.

FIG. 5(a)–(d) illustrate a method of conjugating a stabilized compound and a second compound.

FIG. 6(a)–(d) illustrates site specific conjugation of a stabilized compound with the Fc region of an antibody.

DETAILED DESCRIPTION OF THE INVENTION

I. Definitions

Figure 1A:
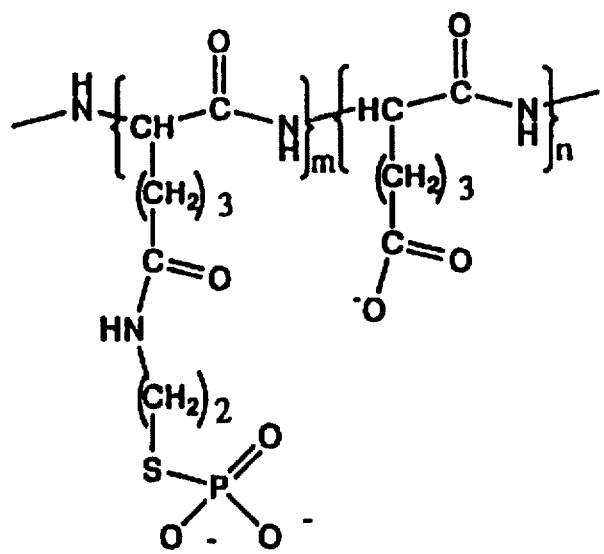
FIG. 1(a)–(f) illustrate crosslinking and conjugation agents.
Figure 1B:
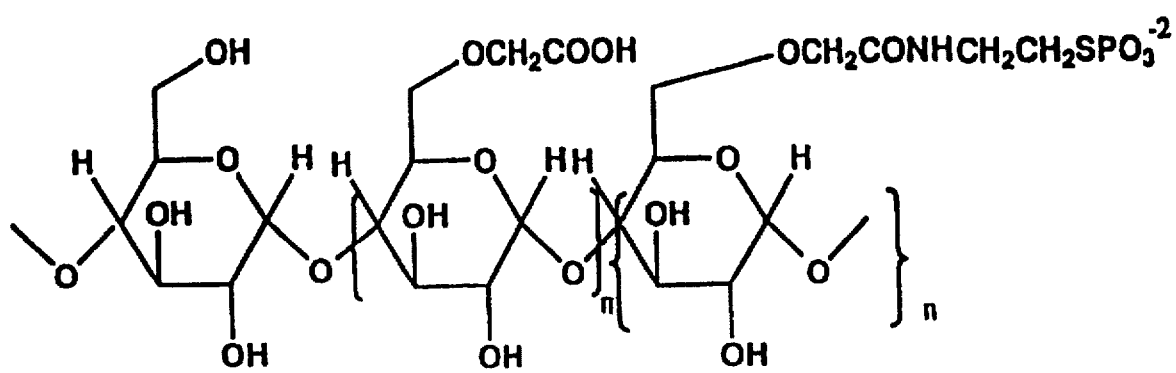
Figure 1C:
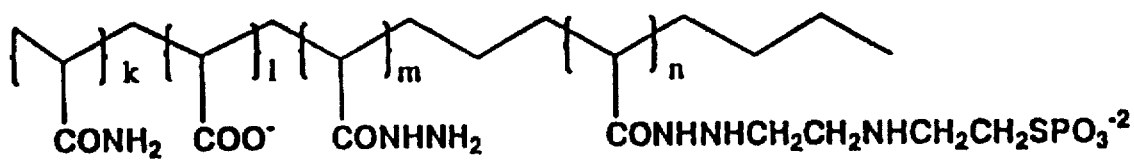
Figure 1D:
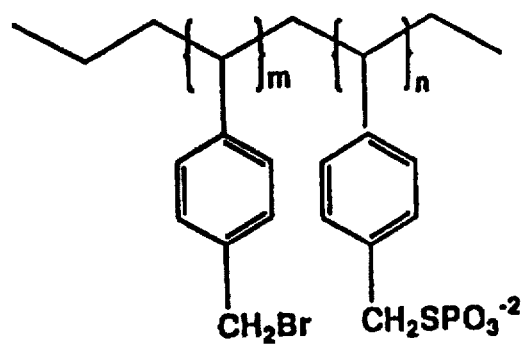
Figure 1E:
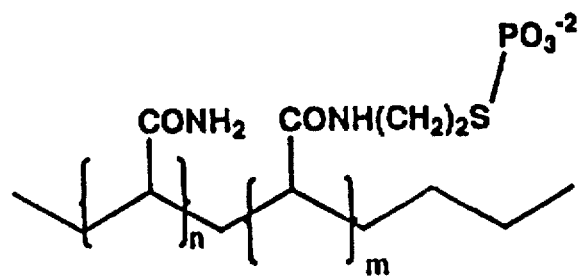
Figure 1F:
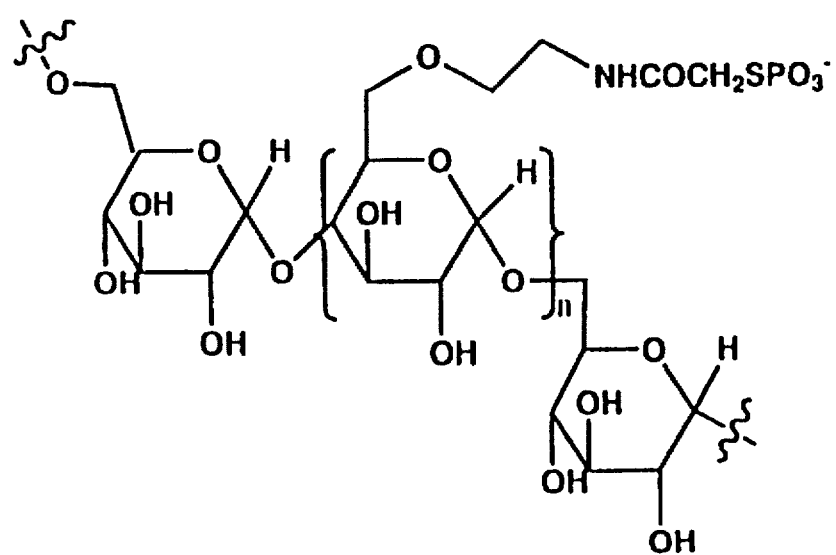
Figures 3A, 3B, 3C:
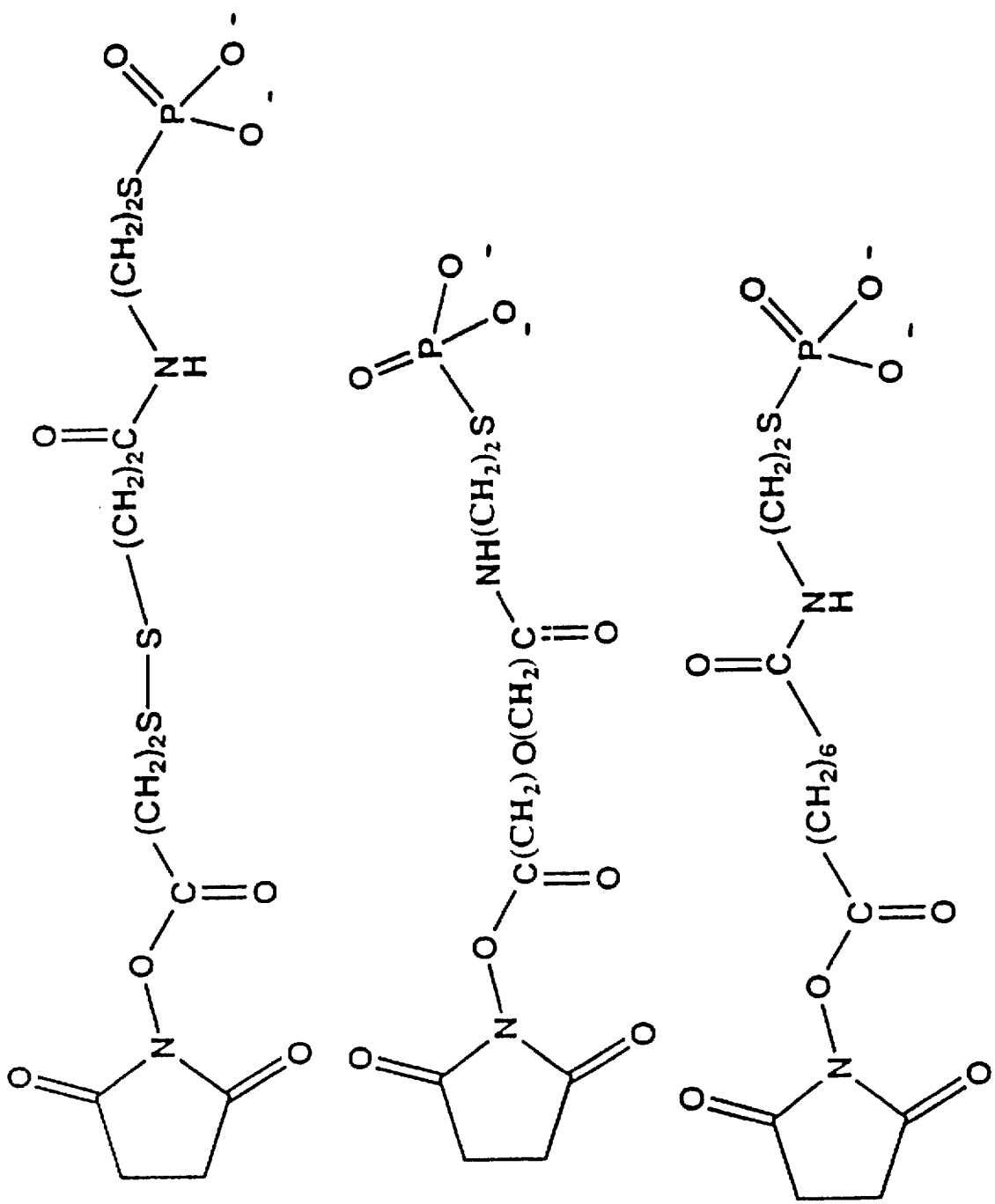
FIG. 3(a)–(f) illustrate heterobifunctional conjugation agents.
Figure 3D:
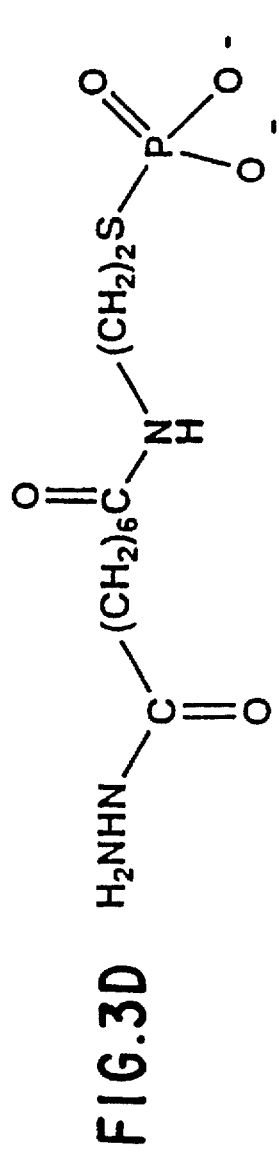
Figure 3E:
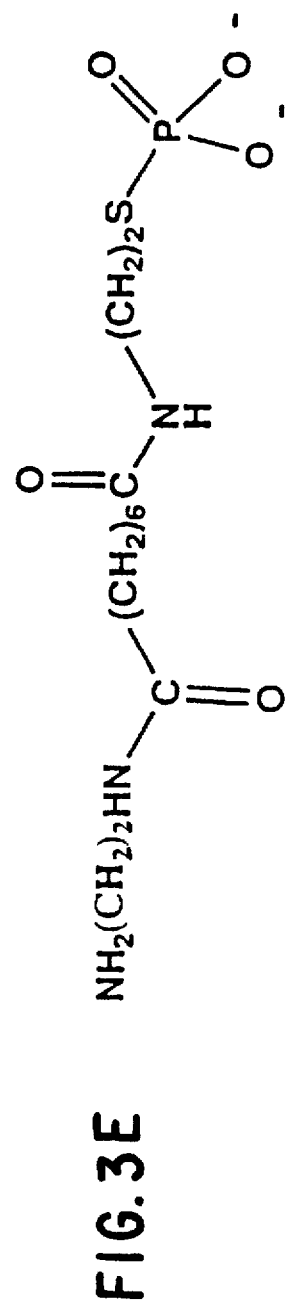
Figure 3F:
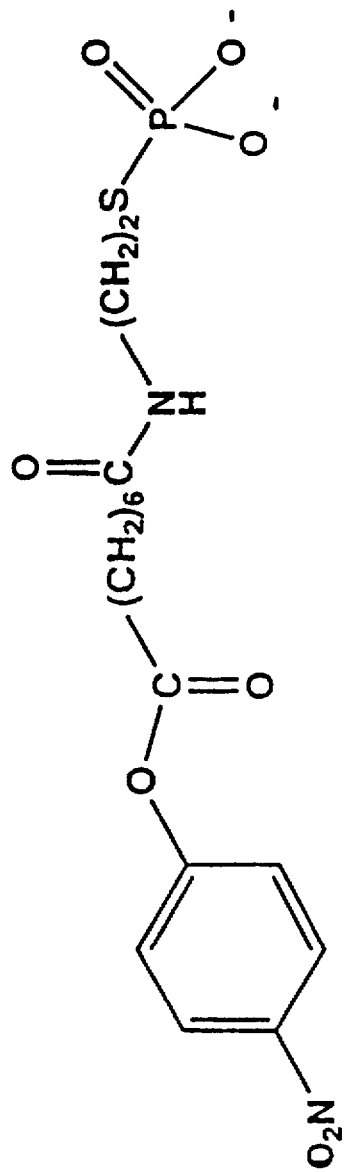

The following definitions are applicable to the invention:

The term "analyte", as used herein, refers to the compound or composition to be detected or measured and which has at least one epitope or binding site. The analyte can be any substance for which there exists a naturally occurring binding member or for which a binding member can be prepared. Analytes include, but are not intended to be limited to, toxins, organic compounds, proteins, peptides, microorganisms, amino acids, carbohydrates, nucleic acids, hormones, steroids, vitamins, drugs (including those administered for therapeutic purposes as well as those administered for illicit purposes), virus particles and metabolites of or antibodies to any of the above substances. For example, such analytes include, but are not intended to be limited to, ferritin; creatinine kinase MB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; IgE antibodies; vitamin B2 micro-globulin; glycated hemoglobin (Gly. Hb); cortisol; digitoxin; N-acetylprocainamide (NAPA); procainamide;

antibodies to rubella, such as rubella-IgG and rubella-IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti hepatitis B core antigen IgG and IgM (Anti-HBC); human immune deficiency virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryoic antigen (CEA); and alpha fetal protein (AFP); and drugs of abuse and controlled substances, including but not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; opiates such as heroin, morphine, codeine, hydromorphone, hydrocodone, methadone, oxycodone, oxymorphone and opium; phencyclidine; and propoxyphene as well as metabolites of the above drugs of abuse and controlled substances. The term "analyte" also includes any antigenic substances, haptens, antibodies, macromolecules and combinations thereof.

"Binding member", as used herein, means a member of a binding pair, i.e., two different molecules where one of the molecules through chemical or physical means specifically binds to the other molecule. In addition to antigen and antibody specific binding pairs, other specific binding pairs include, but are not intended to be limited to, avidin and biotin, carbohydrates and lectins, complementary nucleotide sequences, complementary peptide sequences, effector and receptor molecules, an enzyme cofactor or substrate and an enzyme, an enzyme inhibitor and an enzyme, a peptide sequence and an antibody specific for the sequence or the entire protein, polymeric acids and bases, dyes and protein binders, peptides and specific protein binders (e. g., ribonuclease, S-peptide and ribonuclease S-protein),and the like. Furthermore, binding pairs can include members that are analogs of the original binding member, for example, an analyte-analog or a binding member made by recombinant techniques or molecular engineering. If the binding member is an immunoreactant it can be, for example, a monoclonal or polyclonal antibody, a recombinant protein or recombinant antibody, a chimeric antibody, a mixture(s) or fragment (s) of the foregoing, as well as a preparation of such antibodies, peptides and nucleotides for which suitability for use as binding members is well known to those skilled in the art.

The term "detectable moiety", as used herein, refers to any compound or conventional detectable chemical group having a detectable physical or chemical property and which can be used to label a binding member to form a conjugate therewith. Such detectable chemical group can be, but is not intended to be limited to, enzymatically active groups such as enzymes, enzyme substrates, prosthetic groups or coenzymes; spin labels; fluorescent molecules such as fluorophores and fluorogens; chromophores and chromogens; luminescent molecules such as luminophores, chemiluminophores and bioluminophores; phosphorescent molecules; specifically bindable ligands such as biotin and avidin; electroactive species; radioisotopes; toxins; drugs; haptens; DNA; RNA; polysaccharides; polypeptides; liposomes; colored particles and colored microparticles and the like.

A "solid phase", as used herein, refers to any material which is substantially insoluble. The solid phase can be chosen for its intrinsic ability to attract and immobilize a binding member to form a capture reagent. Alternatively, the solid phase can retain an additional receptor which has the ability to attract and immobilize a binding member to form a capture reagent. The additional receptor can include a charged substance that is oppositely charged with respect to a binding member or to a charged substance conjugated to a binding member. As yet another alternative, the receptor molecule can be any specific binding member which is attached to the solid phase and which has the ability to immobilize another binding member through a specific binding reaction. The receptor molecule enables the indirect binding of a binding member to a solid phase material before the performance of the assay or during the performance of the assay. The solid phase thus can be a latex, plastic, derivatized plastic, magnetic or non-magnetic metal, glass or silicon surface or surfaces of test tubes, microtiter wells, sheets, beads, microparticles, chips, and other configurations known to those of ordinary skill in the art.

It is contemplated and within the scope of the invention that the solid phase also can comprise any suitable porous material with sufficient porosity to allow access by indicator reagents. Microporous structures are generally preferred, but materials with gel structure in the hydrated state may be used as well. Such useful solid supports include: natural polymeric carbohydrates and their synthetically modified, crosslinked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers or the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable.

The term "solid phase reagent", as used herein, means a solid phase to which a binding member has been immobilized. Those skilled in the art will recognize that a binding member can be immobilized to a solid phase through numerous known methods including, for example, any chemical means and/or physical means that does not destroy the specific binding properties of the specific binding member.

As used herein, the term "stable" as well as forms thereof, means that a chemical entity such as, for example, a binding member is efficacious in its environment of use and therefore has or retains at least the chemical and/or biological attributes or activity relevant for its intended use. Thus, for example, if a stabilized compound is a binding member used in an immunoassay, it will have the capacity to bind its complementary binding member to form a binding pair; if a stabilized compound is an enzyme, it will have its enzymatic activity; if the stabilized compound is a detectable moiety, it will have its detectable property. It will be understood, of course, that it is not necessary that a stabilized compound have or retain every chemical attribute as long as the chemical attribute that is not retained is not relevant for its intended use. Additionally, a stabilized compound, as compared to an unstabilized compound, generally resists the loss of its relevant chemical attributes when exposed to environmental stresses such as, for example, temperature extremes, pH extremes and organic solvents. Accordingly, a stabilized compound, as compared to an unstabilized compound, generally retains its relevant chemical attributes for longer periods of time.

The term "test sample", as used herein, refers to a material suspected of containing the analyte. The test sample can be used directly as obtained from the source or following a pre-treatment to modify the character of the sample. The test sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid and the like, and fermentation broths, cell cultures, and chemical reaction mixtures and the like. The test sample can be pretreated prior to use, such as preparing plasma from blood, diluting viscous fluids. and the like. Methods of treatment can involve filtration. distillation, extraction, concentration, inactivation of interfering components, and the addition of reagents. In addition to biological or physiological fluids, other liquid samples can be used such as water, food products and the like for the performance of environmental or food production assays. In addition, a solid material suspected of containing the analyte can be used as the test sample. In some instances, it may be beneficial to modify a solid test sample to form a liquid medium or to release the analyte.

II. Phosphatase Activatable Phosphorothioate Monoester Agents

The present invention provides novel compounds which display at least one phosphorothioate monoester group ($-S-PO_3^{-2}$). It has been discovered that these compounds have utility as (i) crosslinking agents, (ii) conjugation agents, and (iii) reducing agents. Prior to the present invention, compounds were typically crosslinked or conjugated under harsh chemical conditions. Unfortunately, such conditions can damage the chemical and/or biological properties associated with the crosslinked or conjugated compounds. The agents herein provided can be activated and thereafter employed to reduce, crosslink and/or conjugate compounds under gentle conditions. Moreover, the by-products of such reactions are relatively innocuous. Accordingly, a crosslinked compound, for example, does not require purification from the by-products of a crosslinking reaction. Consequently, compounds that are crosslinked, conjugated or reduced, as taught herein, do not run the risk of damage caused by harsh chemical conditions.

A. Crosslinking and Conjugating Agents

Crosslinking and conjugating agents of the present invention generally comprise a monomer, polymer or oligomer backbone that is functional with at least two reactive moieties and at least one of the two reactive moieties comprises a phosphorothioate monoester. The crosslinking agents herein provided have the formula (I), shown below, wherein Q is a straight or branched monomer, polymer or oligomer and n is at least one.

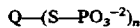
(I)

As previously mentioned, crosslinking and conjugating agents of the present invention will have at least two reactive moieties. Accordingly, when n is one, the monomer, polymer or oligomer backbone will comprise at least one other reactive moiety in addition to the phosphorothioate monoester. Such reactive moieties can include electrophilic and nucleophilic groups such as, for example, haloalkyls, epoxides, hydrazides, hydrazines, thiolates, hydroxyls, and the like, preferably active esters, amines and carboxylic acids.

While the crosslinking and conjugating agents will comprise at least one phosphorothioate monoester group, it is preferred that such agents comprise between about 2 and about 50 phosphorothioate monoester groups, more preferably between about 5 and about 40 phosphorothioate monoester groups and most preferably between about 10 and about 30 phosphorothioate monoester groups.

The crosslinking and conjugating agents herein provided are preferably hydrophilic and display a net negative charge which allows for adequate solubilization of such agents. Accordingly, it is preferred that a crosslinking and conjugating agents backbone is neutral or has a net negative charge. Additionally, it is preferable that the solubility of such agents is at least $1\times10^{-8}M$ at 25° C., more preferably at least $1\times10^{-7}M$ at 25° C., and most preferably at least $1\times10^{-6}M$ at 25° C.

The size of the backbone monomer, polymer or oligomer which comprises a crosslinking and conjugating agent is largely a matter of choice based upon the compound or compounds which are to be crosslinked or conjugated. Preferably the backbone will have an average molecular weight of between about 200 and about 1,000,000, more preferably between about 1,000 and about 850,000, and most preferably between about 2,000 and about 750,000. As it will be understood, of course, the backbone will comprise at least one monomer that is suitable for derivatization with at least one phosphorothioate monoester group. The backbone can be directly functional with the phosphorothioate monoester or the backbone may comprise a phosphorothioate monoester which is pendent from a polymeric side chain or side chains. When present, side chains which may be pendant from the backbone polymer preferably comprise aliphatic chains from 1 to 40 carbon atoms which are optionally substituted with heteroatoms such as, for example, nitrogen (N), oxygen (O), and sulfur (S).

Several monomeric, polymeric or oligomeric backbones have been found to be especially suitable for forming the crosslinking and conjugating agents herein provided. For example, suitable backbones include, but are not intended to be limited to straight or branched polypeptides comprising natural or synthetic amino acid residues such as, for example, polylysine, polyamides, polyglutamic acid, and polyaspartic acid; oligonucleotides such as, for example, DNA and RNA; polycarbohydrates or polysaccharides such as, for example, polyamylose, polyfuranosides, polypyranosides, carboxymethylamylose, and dextrans; polystyrenes such as, for example, chloromethylated polystyrene and bromomethylated polystyrene; polyacrylamides such as, for example, polyacrylamide hydrazide; polyacids such as, for example, polyacrylic acid; polyols such as, for example, polyvinyl alcohol; polyvinyls such as, for example, polyvinyl chloride and polyvinyl bromide; polyesters; polyurethanes; polyolefins; polyethers; $C_5-C_{100,000}$ monomeric or polymeric straight or branched alkyl chains which may optionally contain, within such chains, heteroatoms which may comprise groups such as for example, amines, disulfides, thioethers, active esters, carbamates and the like; $C_{10}-C_{750,000}$ cycloalkyl chains; and the like as well as other monomeric, polymeric or oligomeric materials containing reactive functional groups along the length of their chain which can be substituted with a phosphorothioate monoester group.

Synthesis of the crosslinking and conjugating agents can generally be accomplished by functionalizing a monomer, polymer or oligomer with a phosphorothioate monoester functionality using methodologies which are well known to those skilled in the art. Backbones having, for example, carboxylate functionalities or hydroxyl functionalities such as, for example, polyglutamic acid, polyacrylic acids, carboxymethyl amylose and the like, can be functionalized with phosphorothioate monoester by (i) activating carboxylate or hydroxyl functionalities with a suitable electrophilic activator such as, for example, (1-ethyl 3-(3-dimethylaminopropyl) carbodiimide (EDAC) or bromoacetic acid followed by EDAC and (ii) reacting the so-formed activated esters with cysteamine-S-phosphate. Backbone polymers having haloalkyl styrene residues can be functionalized with a phosphorothioate monoester by reacting a para or ortho phenyl alkyl halide with sodium thiophosphate ($Na_3SPO_3$) as shown below in Scheme I. As it will be understood, of course, any halogenated monomer, polymer or oligomer containing, or which has been modified to contain, a halide may be activated by reacting such polymer with Na$_3$SPO$_3$ in aqueous dimethyl formamide according to Scheme I.

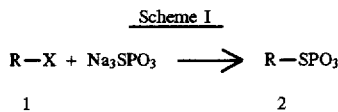

Scheme I

R—X + Na$_3$SPO$_3$ $\longrightarrow$ R—SPO$_3$ 1                          2

Scheme I generally depicts a method disclosed by Bieniarz C., Cornwell M. J., Tetrahedron Lett., 34, 939–942, (1993), for converting a primary or secondary halide to a phosphorothioate monoester. According to Scheme I, the compound of the formula 1, which represents a primary or secondary halide wherein X is a halide, is converted to the corresponding phosphorothioate monoester of the formula 2 using sodium thiophosphate tribasic dodecahydrate or anhydrous sodium thiophosphate in a suitable solvent.

B. Chemical Crosslinking

The crosslinking and conjugating agents of the present invention (which will be referred to as crosslinking agents in this section) can be used to crosslink compounds by activating the crosslinking agent and contacting the activated agent with at least one compound which displays electrophilic and/or nucleophilic groups. According to crosslinking embodiments, multiple covalent bonds are preferably formed between the crosslinking agent and the compound which is crosslinked. As a result, a crosslinked compound is stabilized.

A group of particularly preferred crosslinking agents is shown in FIG. 1. FIG. 1(a) represents poly(glutamic acid) poly(phosphorothioate) wherein m is an integer between about 1 and about 50 and n is an integer between about 1 and about 500; FIG. 1(b) represents carboxymethyl amylose poly(phosphorothioate) wherein m is integer between about 1 and about 500 and n is an integer between about 1 and about 500; FIG. 1(c) represents poly(acrylic acid) poly(hydrazide) poly(phosphorothioate) wherein k is integer between about 1 and about 500, 1 is an integer between about 0 and about 500, m is integer between about 0 and about 500 and n is an integer between about 1 and about 500; FIG. 1(d) represents bromomethylated poly(styrene) poly(phosphorothioate) wherein m is integer between about 1 and about 500 and n is an integer between about 1 and about 100; FIG. 1(e) represents poly(acrylamide) poly(phosphorothioate) wherein m is integer between about 1 and about 500 and n is an integer between about 1 and about 500; and FIG. 1(f) represents dextran poly(phosphorothioate)wherein n is an integer between about 1 and about 500.

Crosslinking agents of the present invention can be activated by deprotecting the thiol group comprising the phosphorothioate monoester. Deprotection generally involves hydrolysis of the phosphate group from the phosphorothioate monoester to expose the nucleophilic thiol group. For example, the thiol group of the phosphorothioate monoester can be deprotected under low pH conditions. Preferably, deprotection in this manner takes place at a pH in the range of between about 4.0 and about 5.5, more preferably in the range of between about 4.5 and about 5.0.

In a particularly preferred embodiment, a phosphate hydrolyzing enzyme (or phosphatase enzyme) is employed to hydrolyze the phosphate protecting group from the phosphorothioate monoester. Because enzymes have very specific catalytic activity, typically, a phosphatase enzyme will only hydrolyze phosphate groups and therefore only react with the crosslinking agent. Hence, compounds that are being crosslinked are not exposed to detrimental chemical conditions. Enzymatically activating a crosslinking agent is typically performed with a catalytic amount of phosphatase enzyme preferably in an amount between about $1 \times 10^{-4}$M and about $1 \times 10^{-14}$M, more preferably between about $1 \times 10^{-6}$M and about $1 \times 10^{-12}$M and most preferably between about $1 \times 10^{-8}$M and about $1 \times 10^{-10}$M. Examples of phosphatase enzymes include but are not intended to be limited to native and recombinant forms of alkaline phosphatase, acid phosphatase and the like.

Upon activation of the crosslinking agent, the highly nucleophilic thiolate groups can react with electrophilic groups displayed by compounds which will be crosslinked. It has been discovered, that by controlling the stoichiometry of the crosslinking agent and the compounds to be crosslinked, efficient crosslinking can be achieved. Surprisingly, reaction conditions can be adjusted so that monomeric, dimeric or trimeric crosslinked compounds are generated and uncontrolled polymerization is substantially mitigated. The ratio of crosslinking agent to compound to be crosslinked is preferably between about 2:1 and about 8:1, and more preferably between about 2:1 and about 4:1.

Generally, proteins (which will be used hereinafter as representative of compounds that can be crosslinked or conjugated) can be functionalized with electrophilic groups through chemical reaction with reactive groups naturally found on proteins such as, for example, —NH$_2$, —SH and the like. Means, G. E. and Feeny, R. E., *Bioconjugate Chemistry*, 1: 2–12 (1990) provides a summary of methodologies for electrophilic addition. Electrophilic groups that can be used to functionalize proteins include, but are not intended to be limited to heterobifunctional linkers such as m-maleimidobenzoyl-N-hydroxysuccinimide ester (MBS), sulfosuccinimidyl 4-(p-maleimidophenyl) butyrate (S-SMPB), m-maleimidobenzoylsulfosuccinimide ester (S-MBS) and N-y-maleimidobutyryloxysuccinimide ester (GMBS), succinimidyl 4-[N-maleimido-methyl] cyclohexane-1-carboxylate (SMCC), and 4-[(N-maleimidomethyl)tricaproamido]-cyclohexane-1-carboxylate (STCM described in U.S. Pat. No. 4,994,385); haloacetyl groups such as iodoacetyl, bromoacetyl, and chloroacetyl; acrylate groups such as methacrylates, quinone groups, and epoxide groups; thiopyridyl groups; as well as other protected disulfides such as, for example, cystamine; transition metal complexes or transition metals in various oxidation states or in colloidal forms which are known to form stable coordinate bonds with thiols such as, for example iron, cobalt, nickel, copper, ruthenium, rhodium, palladium, silver, osmium, iridium, platinum, gold, cadmium and mercury; and the like. Preferably, maleimide groups are used to electrophilically functionalize a protein and most preferably C$_1$–C$_3$ alkyl carboxylic acid active ester maleimides and aryl carboxylic acid active ester maleimides having between about 6 and about 30 atoms between the two terminal functional groups. It will be understood, of course, that a protein may have functionalities that are suitable for reaction with non-phosphorothioate monoester functionalities that are present on the crosslinking agent.

Preferably, a crosslinked protein is "wrapped" or "stitched" by the crosslinking agent as a result of multiple crosslinks which form between the crosslinking agent and the protein. Once wrapped by the polymer, a protein has less conformational freedom and is therefore less likely to undergo structural distortion and in some cases denaturation. Consequently, a crosslinked protein is stabilized. Additionally, a reaction between a nucleophilic group on the crosslinking agent and an electrophilic group on a protein results in the formation of a "linking arm" which spans the distance between a crosslinking agent's backbone and the protein. Preferably, this distance is kept to a minimum to limit a crosslinked compounds conformational freedom.

It is worthy of note that enzymatic activation of a crosslinking agent can be employed in a "self catalyzing reaction." Specifically, the enzyme which catalyzes the activation of the crosslinking agent can be the compound which is to be crosslinked. According to this mechanism, the enzyme can deprotect a crosslinking agent's thiol group or thiol groups which in turn react(s) with the enzyme which unmasked the thiol group or thiol groups. Preferably, the amount of enzyme employed in a self catalyzing reaction is between about $10^{-2}M$ and about $10^{-6}M$.

FIG. 2 generally illustrates crosslinking a protein according to the instant invention. As exemplified by FIG. 2, the protein of FIG. 2(a), which is functional with a plurality of amine groups, can be derivatized with heterobifunctional linkers, such as SMCC, to yield the protein of FIG. 2(b). The crosslinking agent of the instant invention, represented by FIG. 2(c), can be activated with, for example, alkaline phosphatase enzyme to yield the activated crosslinking agent represented by FIG. 2(d). Once activated, the crosslinking agent readily reacts with the electrophilic groups on the protein of FIG. 2(b) to yield the stitched protein of FIG. 2(e).

After a crosslinking reaction is sufficiently complete, the reaction may inherently terminate because there are no further groups capable of reaction, or the reaction may be stopped. A crosslinking reaction can be stopped by capping the exposed thiol groups through the addition of any of the well known thiol capping groups such as, for example, N-ethylmaleimide (NEM), iodoacetamide, iodoacetic acid and the like. Alternatively, one of the reactants can be removed by, for example, passing the reaction mixture over a sizing column. After a stabilized protein is removed from a reaction mixture, unreacted thiol groups, if any, can be capped. As it will be understood, of course, a stabilized protein as represented by FIG. 2(e) can be conjugated to other proteins using unreacted thiolates.

Proteins which are crosslinked as taught herein display an increased stability which can be manifested by, for example, a residual activity that lasts longer than the activity associated with an unstabilized protein and/or a capacity to withstand environmental stress better than an unstabilized protein. For example, a stabilized enzyme may maintain its activity when temperature stressed such as, for example, when the enzyme is stored for 7 days at 45° C. or stored at 25° C. for 30 days. A stabilized enzyme may retain its activity at pHs where the unstabilized enzyme does not have activity. Other potential effects of stabilization may include stability of a protien in an organic solvent which would ordinarily denature an unstabilized protein and enhancement of a binding member's ability to specifically bind and thereby form a binding pair.

C. Conjugating Compounds

The crosslinking and conjugating agents of the present invention can also be employed to conjugate compounds. In this section such agents will be referred to as conjugating agents. According to conjugation embodiments, at least two distinct chemical entities are bound or otherwise immobilized to a conjugating agent. For example, using a conjugating agent, detectable moieties can be immobilized to a binding member to form an indicator reagent, binding members can be immobilized to a chromatographic gel to form affinity chromatographic gels, and binding members can be immobilized to a solid phase to thereby form a solid phase reagent.

While the compounds illustrated in FIG. 1 can be employed as conjugating agents, formulae of heterobifunctional conjugating agents according to the present invention include, but are not limited to, those found in FIG. 3. FIG. 3(a) represents N-hydroxysuccinimidyl cysteamidophosphorothioate 4,5-dithioheptyl 1-carboxylate. FIG. 3(b) represents N-hydroxysuccinimidyl cysteamidophosphorothioate 3-oxybutyl 1-carboxylate. FIG. 3(c) represents N-hydroxysuccinimidyl cysteamidophosphorothioate heptanoyl 1-carboxylate. FIG. 3(d) represents cysteamidophosphorothioate heptanoyl 1-hydrazide. FIG. 3(e) represents cysteamidophosphorothioate heptanoyl 1-(aminoethyl) carboxamide, and FIG. 3(f) represents p-nitrophenyl cysteamidophosphorothioate heptanoyl 1-carboxylate.

Two or more proteins can be conjugated to each other with the conjugation agent herein provided using the same reaction mechanism previously outlined for crosslinking compounds. Specifically, a conjugating agent can be activated under suitable pH conditions or preferably with a phosphatase enzyme. The activated conjugating agent can then be contacted with the proteins to be crosslinked. The nucleophilic thiol groups of an activated conjugating agent react with electrophilic groups present on the compounds to be conjugated to thereby conjugate the compounds. It will be understood, of course, that advantage may be taken of other non-phosphorothioate reactive functionalities displayed by a conjugating agent to conjugate proteins. It will also be understood that compounds may be modified with electrophilic groups, as above, in order to allow them to react with the conjugating agent.

The ratio of reactants in a conjugation reaction are largely dependent upon the final product desired. Thus, for example, if an indicator reagent comprising multiple detectable moieties were desired, the amount of detectable moiety employed in a conjugation reaction would be greater than the amount of either the binding member or conjugation agent employed. Typically, however, the molar ratio of conjugation agent in a conjugation reaction designed to immobilize two compounds is 1:1:1.

The conjugation agent can also be employed in a self catalyzing reaction.

For example, in cases where a phosphate hydrolyzing enzyme is being conjugated, such an enzyme could serve as the activating agent for its own conjugation. Specifically, such an enzyme could hydrolyze the phosphate protecting group from the conjugation agent's phosphorothioate monoester and thereby allow a reaction between the conjugating agent and an electrophilically derivatized enzyme as well as any other electrophilic group functional compound being conjugated.

FIG. 4 generally illustrates the conjugation of multiple compounds using the conjugation agent as a template. As shown by FIG. 4, two proteins which have been functionalized with a maleimide linking group are represented by FIGS. 4(a) and 4(b). The conjugation agent is represented by FIG. 4(c). Upon activation with, for example, a phosphatase enzyme, the thiol groups of the conjugation agent react with the maleimides to form a structure of FIG. 4(d). Hence, the proteins represented by FIGS. 4(a) and 4(b) are conjugated.

As an alternative conjugation, a protein that has been crosslinked can be conjugated with other proteins using the crosslinking agent as a conjugation agent as well. For example, FIG. 5 shows the conjugation of a stabilized protein to an antibody. As shown by FIG. 5, an antibody depicted by FIG. 5(a) can be modified to display a reactive region by, for example, (i) treatment with periodate and (ii) treatment with cystamine and sodium cyanoborohydride to yield an antibody displaying disulphide bridges in the Fc region as depicted by FIG. 5(b). The nucleophilic antibody can then be conjugated to a crosslinked protein, such as that represented by FIG. 5(c), to yield the antibody/stabilized protein conjugate depicted by FIG. 5(d).

Similarly, site specific conjugation of an antibody and a stabilized protein can be performed acccording to FIG. 6 wherein n is less than the number of carbohydrate functionalities present in the Fc region of an antibody. For example, the Fc region of an antibody represented by FIG. 6(a), can be oxidized by periodate and exposed to 4-(N-maleimidomethyl)cyclohexane-1-carboxyl hydrazide ($M_2C_2H$) to yield the the antibody represented by FIG. 6(b). A stabilized protein represented by FIG. 6(c) can then be reacted with the derivatized antibody to site specifically add the stabilized protein to the Fc region of the antibody and yield the conjugate of FIG. 6(d).

Figure 14A:
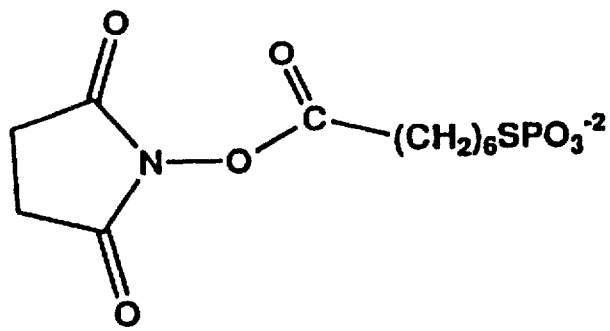
FIG. 14(a)–(e) illustrate the conjugation of two chemical entities using a heterobifunctional conjugation agent.
Figure 14B:
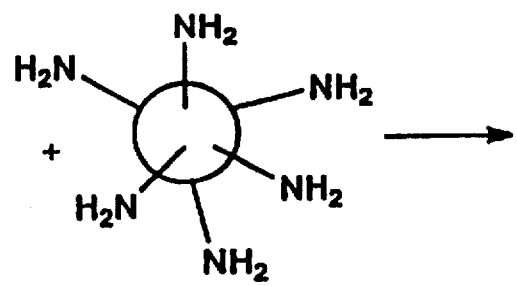
Figure 14C:
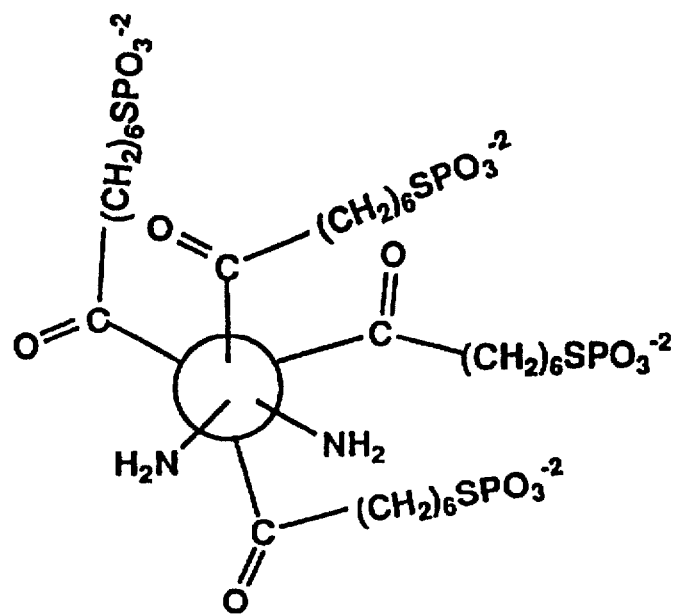
Figure 14D:
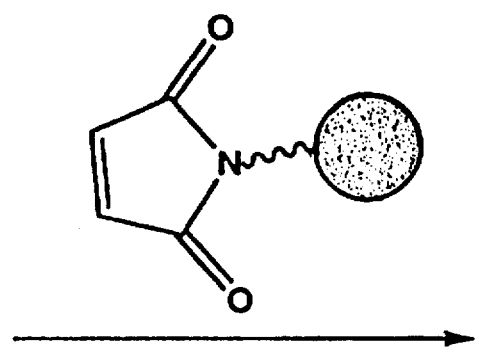
Figure 14E:
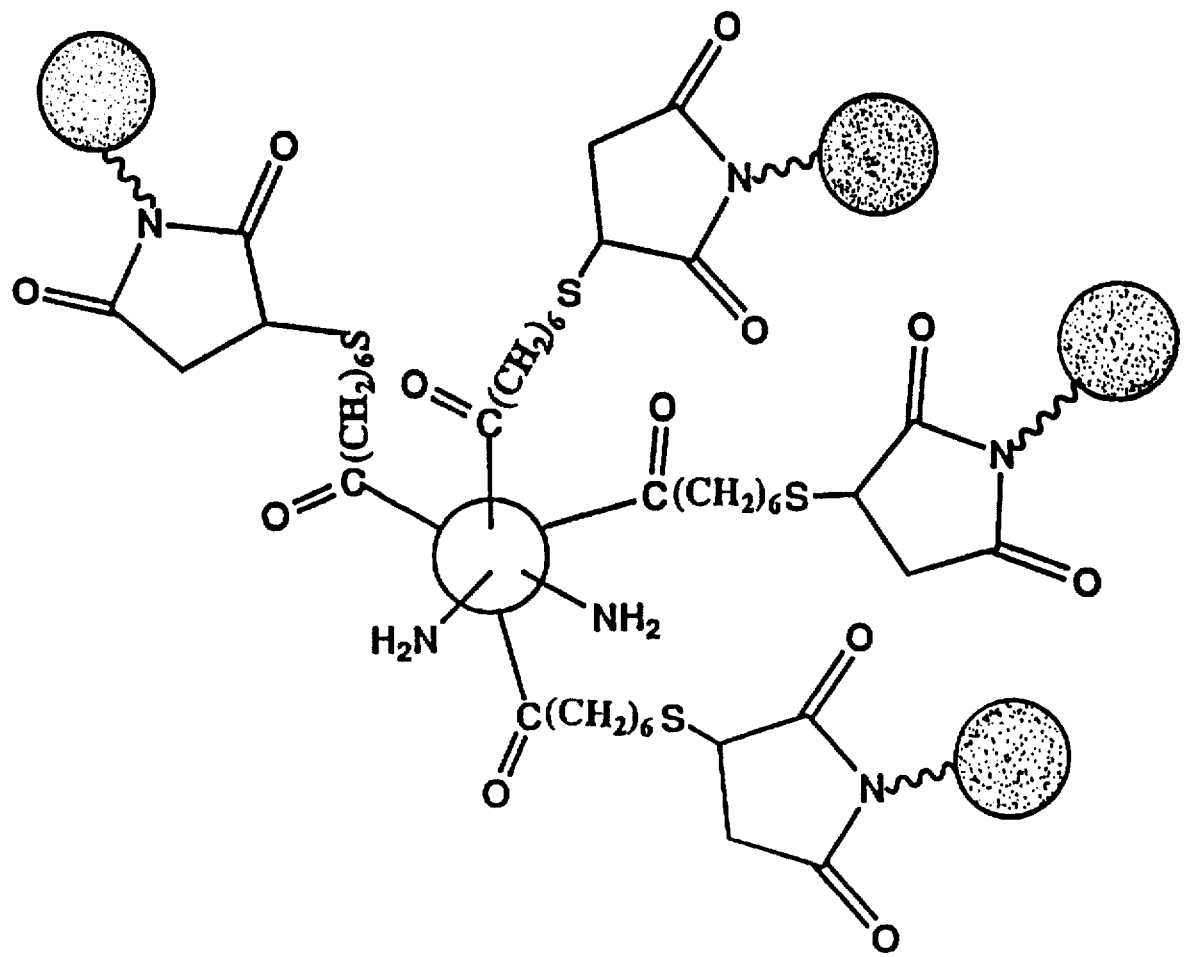

Heterobifunctional conjugating agents such as those represented in FIG. 3(a) through 3(f) can also be employed to conjugate compounds. For example, as shown in FIG. 14, N-hydroxysuccinimidyl cysteamidophosphorothioate heptanoyl 1-carboxylate represented by FIG. 14(a) is reacted under conditions well known to those skilled in the art with an amine functional protein depicted by FIG. 14(b) to yield the protein of FIG. 14(c). A maleimide functional protein shown by FIG. 14(d) is then reacted with the protein of FIG. 14(c) in the presence of, for example, a catalytic amount of alkaline phosphatase. The alkaline phosphatase hydrolyzes the phosphate groups from the heterobifunctional linker which allows a reaction between the nucleophilic thiol group and the electron rich region of the maleimide to yield the conjugated proteins of FIG. 14(e).

D. Reducing Agents

The invention also provides a stabilized reducing agent generally represented by the compound of the formula (Y), shown below, wherein (A) and (Z) can be independently selected from $C_1$–$C_5$ alkyl and $CONH(CH_2)_p$ wherein p is an integer between 1 and 5.

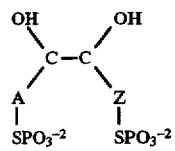

(Y)

Figure 7A:
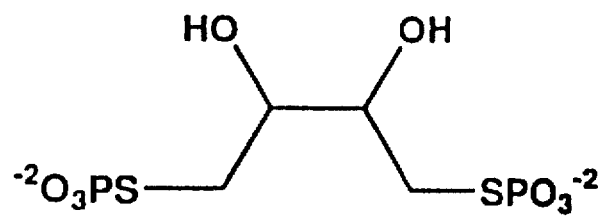
FIG. 7(a)–(b) illustrate stable reducing agents.
Figure 7B:
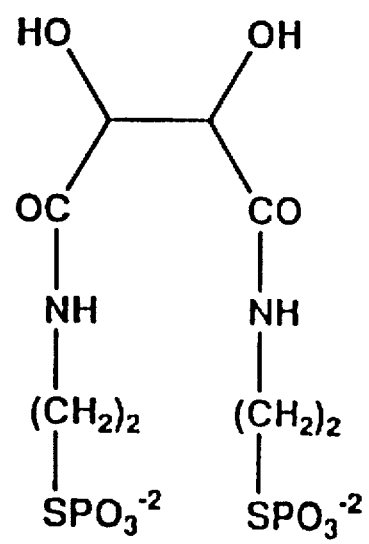

Particularly preferred stable reducing agents are shown in FIG. 7 where the compound designated 7(a) represents dithiothreitol disphosphate and the compound designated 7(b) represents 1,4-bisphosphorothioylethyl tartramide.

The protected reducing agents herein provided can generally be synthesized using methodologies previously described. For example, according to Scheme I, shown above, any primary or secondary halide such as, for example, 1,4-dibromo-2,3 butandiol can be converted to a stabilized reducing agent. As a further example, carboxy functional compounds can be converted to stable reducing agents as previously taught. For instance, tartaric acid can be converted to a stable reducing agent by (i) activating the carboxylates with a suitable electrophilic activator and (ii) reacting the so-formed activated esters with cysteamine-S-phosphate to yield the stabilized reducing agent.

Similarly to the conjugation and crosslinking agents, the thiol groups displayed by the reducing agents are protected and can be activated upon hydrolysis of the phosphate group. Hence, the reducing agents are useful in, for example, containers of liquid or lyophilized immunoassay reagents which require reducing conditions at the time of use. When such a reducing environment is required, the reducing agents can be activated with, for example, a phosphate hydrolyzing enzyme or an appropriate pH environment. After the phosphate groups are hydrolyzed from the phosphorothioate monoester functionalities, a reducing environment results because the thiol groups are no longer protected.

III. Examples

The following examples are provided to further illustrate embodiments of the invention and should not be construed as a limitation on the scope of the invention. The materials employed in the examples are commercially available or readily synthesized. A general compilation of materials and their source can be found in Table 1 below.

TABLE 1

| Source | Source Location | Material Obtained From Source |
|---|---|---|
| Amicon | Beverly, MD | Centriprep-30-Concentrator, Centricon-30-Concentrator |
| Bio-Rad | Hercules, CA | Econo Column, Bio-Sil SEC-400 column, BIO-REX MSZ 501(D) resin |
| Pharmacia LKB | Piscataway, NJ | Pharmacia Phastgel System |
| Spectrum | Houston, TX | All dialysis tubing |
| Hitachi | Naperville, IL | Hitachi F-4010 Fluorescence Spectrophotometer |
| Abbott Laboratories | Abbott Park, IL | Abbott VP Biochromatic Analyzer, horse radish peroxidase (HRPO), 3,5-dichloro-2-hydroxybenzenesulfonic acid sodium salt (HDCBS), 4-aminoantipyrine (4-AAP) |
| Boehringer Mannheim | Indianapolis, IN | bovine alkaline phosphatase (ALP), glucose oxidase (GOD) |
| Yamasa Shoyo | Tokyo, Japan | glutamate oxidase (GlOX) |
| Molecular Probes | Eugene, OR | R-phycoerythrin (R-PE), amino dextran |
| Pierce | Rockford, IL | 3,3'-dithiopropionic acid bis-active ester, SMCC linker, $M_2C_2H$ linker, diglycolic acid bis-active ester, bis-active ester of suberic acid |
| Sigma | St. Louis, MO | Sephadex G-25, N-ethylmaleimide (NEM), succinimidyl bromoacetate, sodium thiophosphate, poly-L-glutamic acid, cysteamine-S-phosphate, EDAC, carboxymethylamylose, sodium m-periodate, sodium cyanoborohydride, glucose, polyacrylamide hydrazide, p-nitrophenyl phosphate (PNPP), bovine serum albumin, ethylenediaminetetraacetic acid (EDTA) |
| Seradyne | Indianapolis, IN | aminated microparticles |
| Aldrich | Milwaukee, WI | hydrazine monohydrate, ethylenediamine, poly(acrylamide-co-acrylic acid), 5,5'-dithio-bis(2-nitrobenzoic acid) (DTNB), glyceraldehyde, kathon, 1,4-dibromo-2,3-butanediol, silver nitrate, paranitrophenol, dithiothreitol (DTT) |

EXAMPLE 1

Synthesis of Poly(phosphorothioate) Functionalized Polymers (a) Poly(glutamic acid) Poly(phosphorothioate)

Poly-L-glutamic acid MW~70,000 (1.0 g, 14 μmol) and cysteamine-S-phosphate (0.26 g, 1.4 mmol) were dissolved in 40 ml of deionized water. EDAC (1.00 g, 5.2 mmol) was added in 100 mg lots every 30 minutes for 5 hours. The polymer product was purified with a Centriprep-30-concentrator against deionized water and then lyophilized.

(b) Phosphorothioate Analysis

To 1.0 ml of a 5.0 μM solution of poly(glutamic acid) poly(phosphorothioate) in 0.1M Tris buffer, 1.0 mM $MgCl_2$, 0.1 mM $ZnCl_2$, pH 7.5 (Buffer A) was added 30 μl of DTNB (10 mM in buffer A). The solution was incubated for 5 minutes and the absorbance at 412 nm was recorded. No free thiol was detected. ALP (10 µl of a 10 mg/ml solution) was added and the solution was incubated until no further increase in 412 nm absorbance was detected (~30 minutes). The concentration of free thiol (0.12 mM) was calculated from the final 412 nm absorbance (1.54 AU) and the extinction coefficient of 2-nitro-5-thiobenzoic acid (13,000M-1cm-1 at pH 7.5). There were found to be 24 moles of phosphorothioate per mole of polymer.

(c) Carboxymethylamylose Polyphosphorothioate

Carboxymethylamylose MW~60,000 (0.15 g, 2.5 µmol) and cysteamine-S-phosphate were dissolved in 10 ml of deionized water. EDAC (0.125 g, 0.65 mmol) was added in 25 mg lots every hour for 5 hours. The carbohydrate product was purified on a Centriprep-30-Concentrator against deionized water and then lyophilized. Phosphorothioate analysis (performed as described above) revealed 1 phosphorothioate per carboxymethylamylose polymer chain.

(d) Poly(acrylamide) Poly[acryloyl(2-(2-phosphorothioethyl)aminoethyl] Hydrazide Polyacrylamide hydrazide MW~180,000 (0.050 g, 0.28 µmol) was dissolved in 20 ml of 0.05M sodium acetate buffer pH 4.5 (buffer B). Glyceraldehyde (0.080 g, 0.89 mmol) and sodium cyanoborohydride (0.056 g, 0.89 mmol) were added and the solution was stirred for 20 hours. The polydiol product was purified on a Centriprep-30-Concentrator against buffer B. Sodium periodate (0.095 g, 4.4 mmol) in 10 ml of buffer B was added to the polydiol and the mixture was stirred for 1 hour in an ice-bath, allowed to warm to room temperature, and stirred again for another hour. The polyaldehyde product was purified on a Centriprep-30-Concentrator against 0.1M sodium phosphate buffer pH 5.5.

To the polyaldehyde was added cysteamine-S-phosphate (0.079 g, 0.44 mmol) and sodium cyanoborohydride (0.028 g, 0.44 mmol) and the mixture was stirred overnight. The polyphosphorothioate product was purified on a Centriprep-30-Concentrator against deionized water and then lyophilized. Phosphorothioate analysis (performed as described above) revealed 66 phosphorothioates per polymer.

(e) Poly(amino)dextran Poly(phosphorothioate)

Amino dextran (MW~70,000, approximately 30 amines/polymer) is dissolved in deionized water. 20 equivalents of succinimidyl bromoacetate is dissolved in dimethylformamide (DMF) and a volume of this solution which is greater than 10% of the amino dextran solution is added to the amino dextran solution to form a reaction mixture. The reaction mixture is stirred for 3 hours at room temperature and the resulting bromoacetylated polymer is purified against deionized water with a Centriprep-30-Concentrator. 50 equivalents of sodium thiophosphate in deionized water is then added to the purified polymer and the resulting mixture is stirred for 2 hours at room temperature. The resulting phosphorothioated amino dextran is purified, as above, with a Centriprep-30-Concentrator and lyophilized.

(f) Poly(acrylamide-co-acrylic acid) Poly(phosphorothioate)

Poly(acrylamide-co-acrylic acid) MW~200,000 (1.0 g, 5 µmol) and cysteamine-S-phosphate (0.09 g, 0.5 mmol) are dissolved in 40 ml of deionized water. EDAC (0.5 g, 2.6 mmol) is added in 50 mg lots every 30 minutes for 5 hours. The polymer product is purified on a Centriprep-30-concentrator against deionized water and then lyophilized.

EXAMPLE 2

Poly(glutamic acid) Poly(phosphorothioate) Crosslinking of Bovine Alkaline

Phosphatase (ALP)

(a) Crosslinking of Alkaline Phosphatase

To 0.75 ml of 10 mg/ml (50 nmol) ALP was added 1.25 ml of 0.1M sodium phosphate, 0.1 M NaCl, 1.0 mM $MgCl_2$, 0.1 mM $ZnCl_2$, pH 7.0 (buffer C). The enzyme was concentrated to approximately 0.2 ml using a Centricon-30-Concentrator. The concentrate was rediluted to 2.0 ml with buffer C, then reconcentrated to 0.2 ml. This concentration/dilution procedure was repeated three times. The volume of the enzyme solution was made up to 1.5 ml with buffer C and placed in a vial. To 75 µl of DMF was added 0.62 mg (1.87 µmol) of SMCC. This solution was added to 1.46 ml of 4.8 mg/ml (46.7 nmol) washed alkaline phosphatase and allowed to react for one hour at room temperature while rotating at 100 rpm on a rotary agitator. Coarse Sephadex G-25 that had been previously rehydrated with 0.1M sodium phosphate, 0.1M NaCl, 0.05% azide, pH 7.0 (buffer D) was poured to a bed height of 45 cm in a 1×50 cm Econo column. The column was equilibrated with three column volumes of buffer C. Following the incubation, the SMCC derivatized alkaline phosphatase was applied to the G-25 column to remove unreacted SMCC. The column was eluted with buffer C and 0.75 ml fractions were collected. Fractions with $A_{280}$ greater than 0.5 AU were pooled and the $A_{280}$ of the pool was used to calculate the enzyme concentration of the SMCC derivatized alkaline phosphatase. To 300 µl of buffer C was added 2.43 mg (34.7 nmol) of 70,000 MW poly (glutamic acid) poly(phosphorothioate) (26 SPO3/PGA). This solution was added to 1.86 ml of 1.40 mglml (17.4 nmol) SMCC derivatized alkaline phosphatase and allowed to react overnight at 5° C. while rotating at 100 rpm on a rotary agitator.

(b) Characterization of Crosslinked ALP

Poly(glutamic acid) poly(phosphorothioate) crosslinked ALP was evaluated by size exclusion chromatography using a Bio-Sil SEC-400 column. Detection was at 280 nm. The mobile phase was 0.1M sodium phosphate, 0.1M NaCl, pH 7.0 (buffer E) running at a flow rate of 1.0 ml/minute. Results of this evaluation showed that the primary population generated had a retention time corresponding to singlet crosslinked enzyme with very little polymerization occurring. The crosslinked alkaline phosphatase was also evaluated by SDS-PAGE using a Phastgel system. Gradient gels of 7%-10% polyacrylamide were run under non-reducing and reducing conditions. Results from the non-reducing conditions showed that the primary population generated was singlet crosslinked enzyme with very little polymerization occurring. Results from the reducing conditions showed that the crosslinked ALP was not reduced under conditions that were sufficient to fully reduce the native ALP into monomers. The residual enzyme activity of the crosslinked ALP was evaluated and compared to the activity of the native ALP at the same concentration. To 1.0 ml of 7 mM PNPP in 0.5M diethanolamine, 1.0 mM $MgCl_2$, 0.1 mM $ZnCl_2$, pH 10.2 buffer (buffer F) was added 20 µl of 10 µg/ml ALP. The rate (AU/second) of change in the 412 nm absorbance was calculated over a 14 second interval. The rate generated by the crosslinked ALP preparations was divided by the rate generated by the native ALP to calculate the percent residual enzyme activity for the crosslinked preparations. The results of this evaluation showed that the crosslinked ALP had retained 80% of the initial enzyme activity.

(c) Thermal Stability Evaluation of Crosslinked ALP

Figure 8:
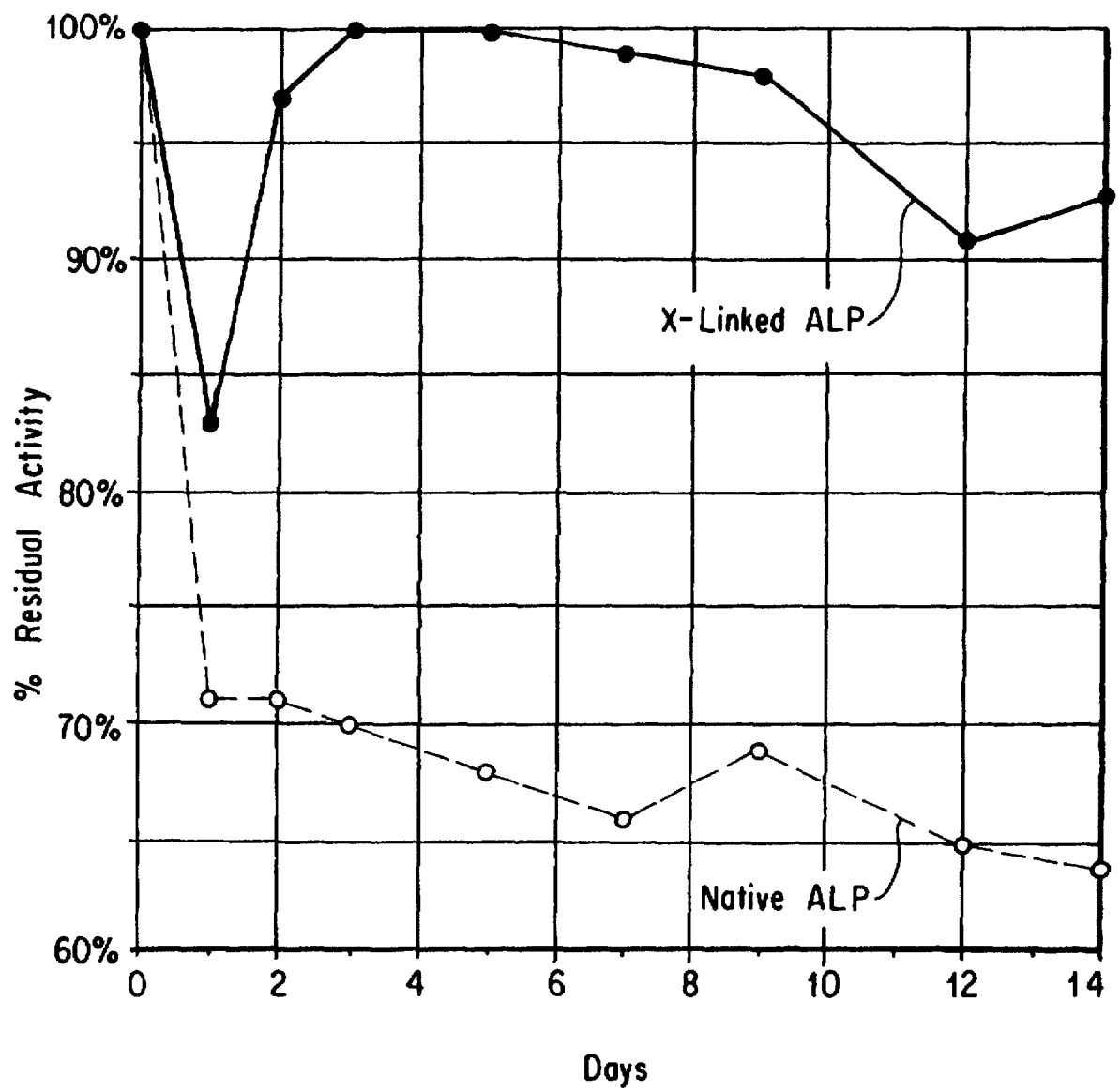
FIG. 8–13 graphically illustrate the various property improvements displayed by stabilized compounds.

The thermal stability of poly(glutamic acid) poly (phosphorothioate) crosslinked ALP was evaluated at 45° C. and compared to native ALP under the same conditions. Both the native enzyme and the crosslinked enzyme were diluted to 10 µg/ml with buffer A. These dilutions were stored in a 45° C. incubator for the duration of the study. At day 0 and various time points along the course of the study the activity of the dilutions was evaluated. To separate 1.0 ml volumes of 7 mM PNPP in buffer F was added 20 µl of the 10 µg/ml ALP dilutions. The rate of change in the 412 nm absorbance was calculated over a 14 second interval. The rate generated by the enzyme preparations at the various time points was divided by the rate generated by the same enzyme preparation at day 0 to calculate the percent residual enzyme activity for the stressed preparations. The results of this evaluation are shown in FIG. 8.

EXAMPLE 3

Poly(glutamic acid) Poly(phosphorothioate) Crosslinking of Glucose Oxidase (GOD) (Aspergillus niger)

(a) Crosslinking GOD

To 200 mg (1.25 µmol) of GOD was added 20 ml of buffer E. The enzyme was concentrated to approximately 2 ml using a Centriprep-30-Concentrator with a MW cutoff of 30,000. The concentrate was rediluted to 20 ml using buffer E then reconcentrated to 2 ml. This concentration/dilution procedure was repeated three times. The volume of the enzyme solution was made up to 6 ml with buffer E and placed in a vial. To 500 µl of DMF was added 9.39 mg (28.1 µmol) of SMCC. This solution was added to a 977 µl aliquot of 30.7 mg/ml (187 nmol) washed GOD and allowed to react for one hour at room temperature while rotating at 100 rpm on a rotary agitator. A Sephadex G-25 was prepared as above with buffer E, and following the incubation, the SMCC derivatized GOD was applied to the G-25 column to remove the unreacted SMCC. The column was eluted with buffer E and 0.75 ml fractions were collected. Fractions with an $A_{280}$ greater than 0.5 AU were pooled and the $A_{280}$ of the pool used to calculate the enzyme concentration of the SMCC derivatized GOD. To 1.5 ml of buffer C was added 56.3 mg (938 nmol) of 60,000 MW poly(glutamic acid) poly (phosphorothioate) (19 SPO3/PGA). To this solution was added 50 µl of 10 mg/ml (3.33 nmol) ALP to deprotect the phosphorothioate. This deprotection was allowed to proceed for three hours at room temperature while rotating at 100 rpm on a rotary agitator. Following the incubation a 300 µl (188 nmol) aliquot of this solution was added to 1.26 ml of 7.95 mg/ml (62.6 nmol) SMCC derivatized GOD and allowed to react overnight at 5° C. while rotating at 100 rpm on a rotary agitator.

(b) Characterization of Crosslinked GOD

Poly(glutamic acid) poly(phosphorothioate) crosslinked GOD was evaluated by size exclusion chromatography using a Bio-Sil SEC-400 column. Detection was at 280 nm. The mobile phase was buffer E running at a flow rate of 1.0 ml/minute. Results of this evaluation showed that the primary population generated had a retention time corresponding to singlet crosslinked enzyme with very little polymerization occurring. The residual enzyme activity of the crosslinked GOD was also evaluated and compared to the activity of the native GOD at the same concentration. To 260 µl of 2 mM 4-aminoantipyrine (4-AAP), 8 mM 2-hydroxy-3,5 dichlorobenzene acid (HDCBS), 1 U/ml horseradish peroxidase (HRPO) and 100 mM glucose, in buffer E was added 10 µl of 2 µg/ml GOD in buffer E. The rate (AU/minute) of change in the 550 nm absorbance was calculated over a 2 minute interval. The rate generated by the crosslinked GOD preparations was divided by the rate generated by the native GOD to calculate the percent residual enzyme activity for the crosslinked preparations. The results of this evaluation showed that the crosslinked GOD had retained 85% of the initial enzyme activity.

(c) Thermal Stability Evaluation of Crosslinked GOD at pH 7.4

The thermal stability of poly(glutamic acid) poly (phosphorothioate) crosslinked GOD was evaluated at 37° C. and compared to native GOD under the same conditions. Both the native enzyme and the crosslinked enzyme were diluted to 500 µg/ml with 0.1M sodium phosphate, 1.0 mM EDTA, 0.1M NaCl, 0.05% Kathon, pH 7.4 buffer (buffer G). These dilutions were stored in a 37° C. incubator for the duration of the study. At day 0 and various time points along the course of the study the activity of both preparations was evaluated.

Figure 9:
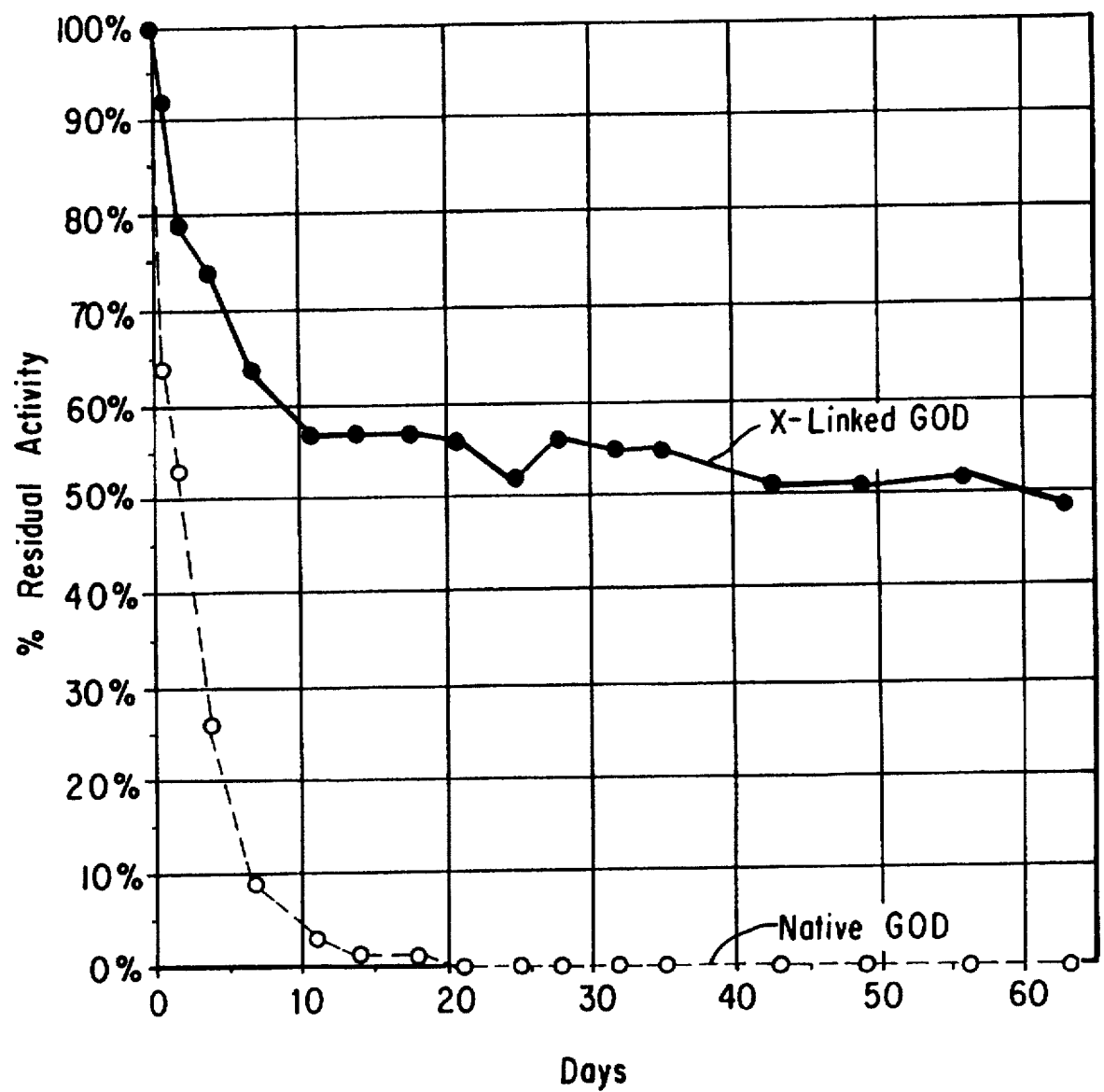

Prior to evaluation, the stressed enzyme preparations were diluted to 2 µg/ml using buffer E. To 260 µl of 2 mM 4-AAP, 8 mM HDCBS, 1 U/ml HRPO, 100 mM glucose in buffer E was added 10 µl of each of the 2 µg/ml glucose oxidase in buffer E dilutions. The rate (AU/minute) of change in the 550 nm absorbance was calculated over a 2 minute interval. The rate generated by the enzyme preparations at the various time points was divided by the rate generated by the same enzyme preparation at day 0 to calculate the percent residual enzyme activity for the stressed preparations. The results of this evaluation are shown in FIG. 9.

(d) Thermal Stability Evaluation of Crosslinked GOD at pH 9.0

Figure 10:
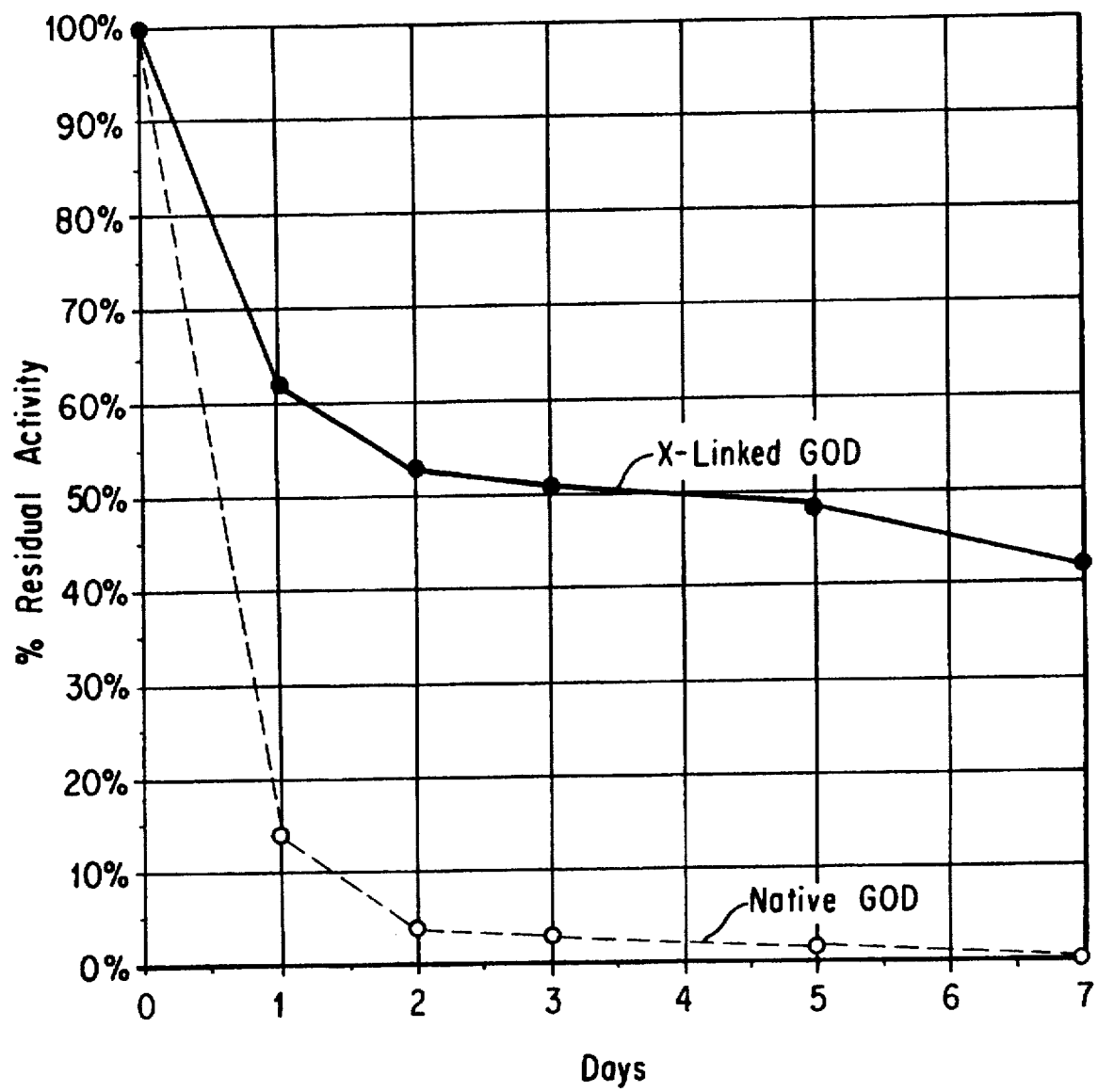

The thermal stability of poly(glutamic acid) poly (phosphorothioate) crosslinked GOD was evaluated at 37° C. and compared to native GOD under the same conditions. Both the native enzyme and the crosslinked enzyme were diluted to 500 µg/ml with 0.1M sodium phosphate, 1.0 mM EDTA, 0.1M NaCl, 0.05% Kathon, pH 9.0 buffer (buffer H). These dilutions were stored in a 37° C. incubator for the duration of the study. At day 0 and various time points along the course of the study the activity of both preparations was evaluated. Prior to evaluation the stressed enzyme preparations were diluted to 2 µg/ml using buffer E. To 260 µl of 2 mM 4-AAP, 8 mM HDCBS, 1 U/ml HRPO, 100 mM glucose in buffer E was added 10 µl of each of the 2 µg/ml GOD dilutions. The rate (AU/minute) of change in the 550 nm absorbance was calculated over a 2 minute interval. The rate generated by the enzyme preparations at the various time points was divided by the rate generated by the same enzyme preparation at day 0 to calculate the percent residual enzyme activity for the stressed preparations. The results of this evaluation are shown in FIG. 10.

EXAMPLE 4

Poly(glutamic acid) poly(phosphorothioate) Crosslinking of Glutamate Oxidase (GlOX) (Streptomyces Sp. X119-6)

(a) Crosslinking of GlOX

To 100 mg (714 mnol) of GlOX was added 20 ml of buffer E. This solution was concentrated to approximately 2 ml using a Centriprep-30-Concentrator with a MW cutoff of 30,000. The concentrate was rediluted to 20 ml with buffer E then reconcentrated to 2 ml. This concentration/dilution procedure was repeated three times. The volume of the enzyme solution was made up to 3 ml with buffer E and placed in a vial. To 800 µl of DMF was added 4.18 mg (12.5 µgmol) of SMCC. This solution was added to a 1.25 ml aliquot of 28.0 mg/ml (250 nmol) washed GlOX and allowed to react for one hour at room temperature while rotating at 100 rpm on a rotary agitator. A Sephadex G-25 column was prepared as above using buffer E, and following the incubation, the SMCC derivatized GlOX was applied to the G-25 column to remove the unreacted SMCC. The column was eluted with buffer E and 0.75 ml fractions were collected. Fractions with an $A_{410}$ greater than 1.0 AU were pooled and the $A_{410}$ of the pool was from used to calculate the enzyme concentration of the SMCC derivatized GlOX. To 2.5 ml of buffer C was added 100 mg (1.67 µmol) of 60,000 MW poly(glutamic acid) poly(phosphorothioate) (18 SPO3/PGA). To this solution was added 50 µl of 10 mg/ml (3.33 nmol) ALP to deprotect the phosphorothioate. The deprotection was allowed to proceed for three hours at room temperature while rotating at 100 rpm on a rotary agitator. Following the incubation, a 524 µl (343 nmol) aliquot of this solution was added to 1.74 ml of 6.88 mg/ml (85.5 nmol) SMCC derivatized GlOX and allowed to react overnight at 5° C. while rotating at 100 rpm on a rotary agitator.

(b) Characterization of Crosslinked GlOX

Poly(glutamic acid) poly(phosphorothioate) crosslinked GlOX was evaluated by size exclusion chromatography using a Bio-Sil SEC-400 column. Detection was at 410 nm. The mobile phase was buffer E running at a flow rate of 1.0 ml/minute. Results of this evaluation showed that the primary population generated had a retention time corresponding to doublet and triplet crosslinked enzyme with very little polymerization occurring. The residual enzyme activity of the crosslinked GlOX was also evaluated and compared to the activity of the native GlOX at the same concentration. Activity measurements were performed using a VP bichromatic analyzer. The activity generated by the crosslinked GlOX preparations was divided by the activity of the native GlOX to calculate the percent residual enzyme activity for the crosslinked preparations. The results of this evaluation showed that the crosslinked GlOX had retained 81% of the initial enzyme activity.

(c) Thermal Stability Evaluation of Crosslinked GlOX

Figure 11:
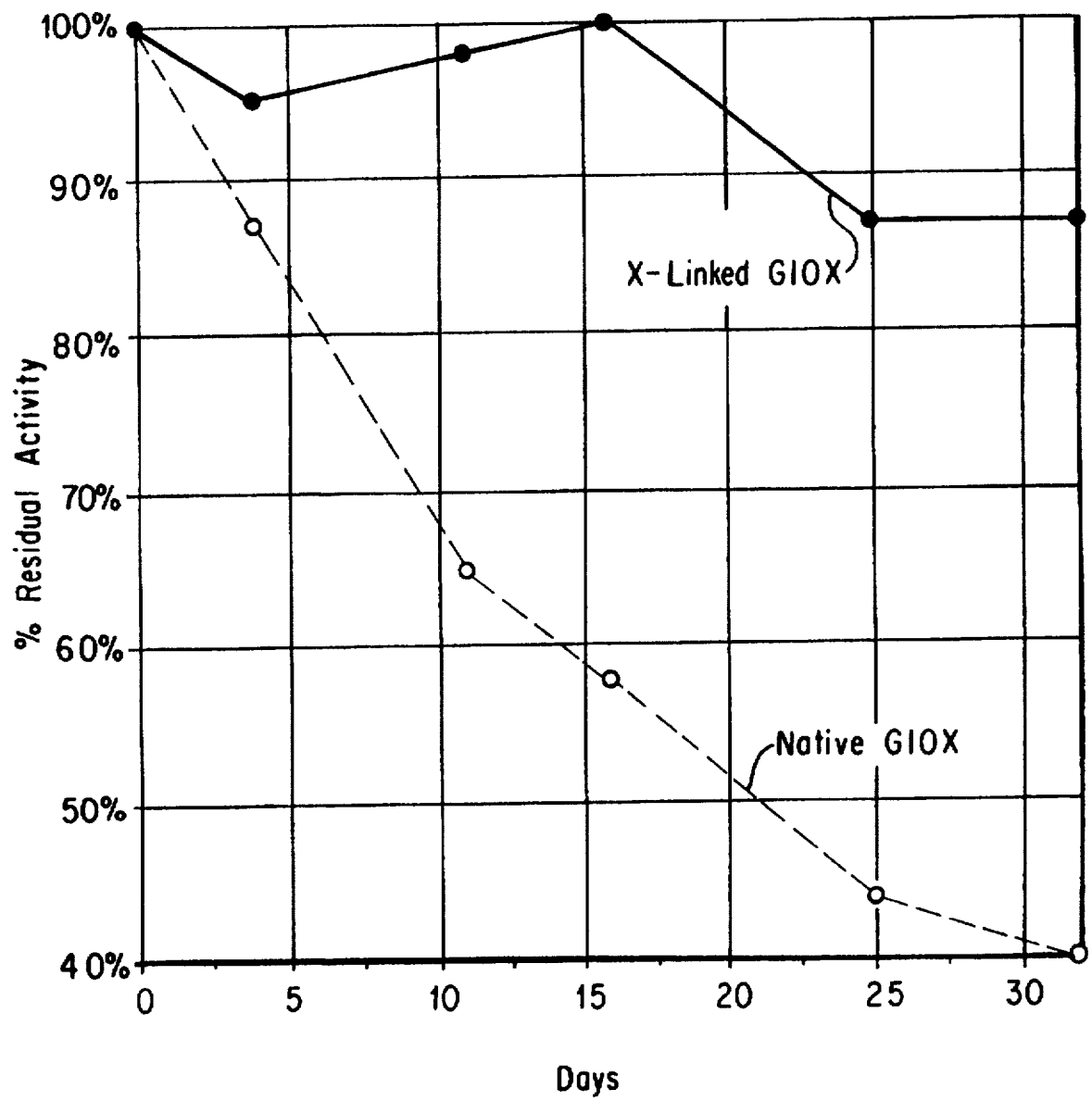

The thermal stability of poly(glutamic acid) poly (phosphorothioate) crosslinked GlOX was evaluated at 37° C. and compared to native GlOX under the same conditions. Both the native enzyme and the crosslinked enzyme were diluted to 500 µg/ml with buffer G. These dilutions were stored in a 37° C. incubator for the duration of the study. At day 0 and various time points along the course of the study the activity of both preparations was evaluated. Prior to evaluation, the stressed enzyme preparations were diluted to 6 µg/ml using buffer E. Activity measurements were performed using the VP bichromatic analyzer. The activity generated by the enzyme preparations at the various time points was divided by the activity generated by the same enzyme preparation at day 0 to calculate the percent residual enzyme activity for the stressed preparations. The results of this evaluation are shown in FIG. 11.

EXAMPLE 5

Poly(glutamic acid) Poly(phosphorothioate) Crosslinking of R-phycoerythrin (R-PE) (Porphyra tenera)

(a) Crosslinking of R-PE

To 2.5 ml of 10 mg/ml R-PE from was added 2 ml of buffer E. This solution was transferred to Spectrapore-2 dialysis tubing with a MW cutoff of 12,000–14,000 and dialyzed for 24 hours each against three 4 liter changes of buffer E. To 200 µl of DMF was added 0.49 mg (1.47 µgmol) of SMCC. This solution was added to a 1.21 ml aliquot of 5.80 mg/ml (29.2 nmol) dialyzed R-PE and allowed to react for one hour at room temperature while rotating at 100 rpm on a rotary agitator. A Sephadex G-25 column was prepared as above with buffer E, and following the incubation, the SMCC derivatized R-PE was applied to the G-25 column to remove unreacted SMCC. The column was eluted with buffer E and 0.75 ml fractions were collected. Fractions with an $A_{566}$ greater than 1.0 AU were pooled and the A566 of the pool was used to calculate the enzyme concentration of the SMCC derivatized R-PE. To 1 ml of buffer C was added 10 mg (167 nmol) of 60,000 MW poly(glutamic acid) poly (phosphorothioate) (18 SPO3/PGA). To this solution was added 25 µl of 10 mg/ml (1.67 nmol) ALP to deprotect the phosphorothioate. This deprotection was allowed to proceed for three hours at room temperature while rotating at 100 rpm on a rotary agitator. Following the incubation, a 71 µl (11.5 nmol) aliquot of this solution was added to 1.91 ml of 1.44 mg/ml (11.5 nmol) SMCC derivatized R-PE and allowed to react overnight at 5° C. while rotating at 100 rpm on a rotary agitator.

(b) Characterization of Crosslinked R-PE

Poly(glutamic acid) poly(phosphorothioate) crosslinked R-PE was evaluated by size exclusion chromatography using a Bio-Sil SEC-400 column. Detection was at 280 nm. The mobile phase was buffer E running at a flow rate of 1.0 ml/minute. Results of this evaluation showed that the primary population generated had a retention time corresponding to singlet and doublet crosslinked protein with very little polymerization occurring. The residual fluorescent intensity of the crosslinked R-PEwas also evaluated and compared to the fluorescence of the native R-PE at the same concentration. Fluorescent intensity measurements were performed using an F-4010 fluorescence spectrophotometer. The fluorescence generated by the crosslinked R-PE preparations was divided by the fluorescence of the native R-PE to calculate the percent residual fluorescence for the crosslinked preparations. The results of this evaluation showed that the crosslinked R-PE had retained 92% of the initial fluorescent intensity.

(c) Thermal Stability Evaluation of Crosslinked R-PE Fluorescence

Figure 12:
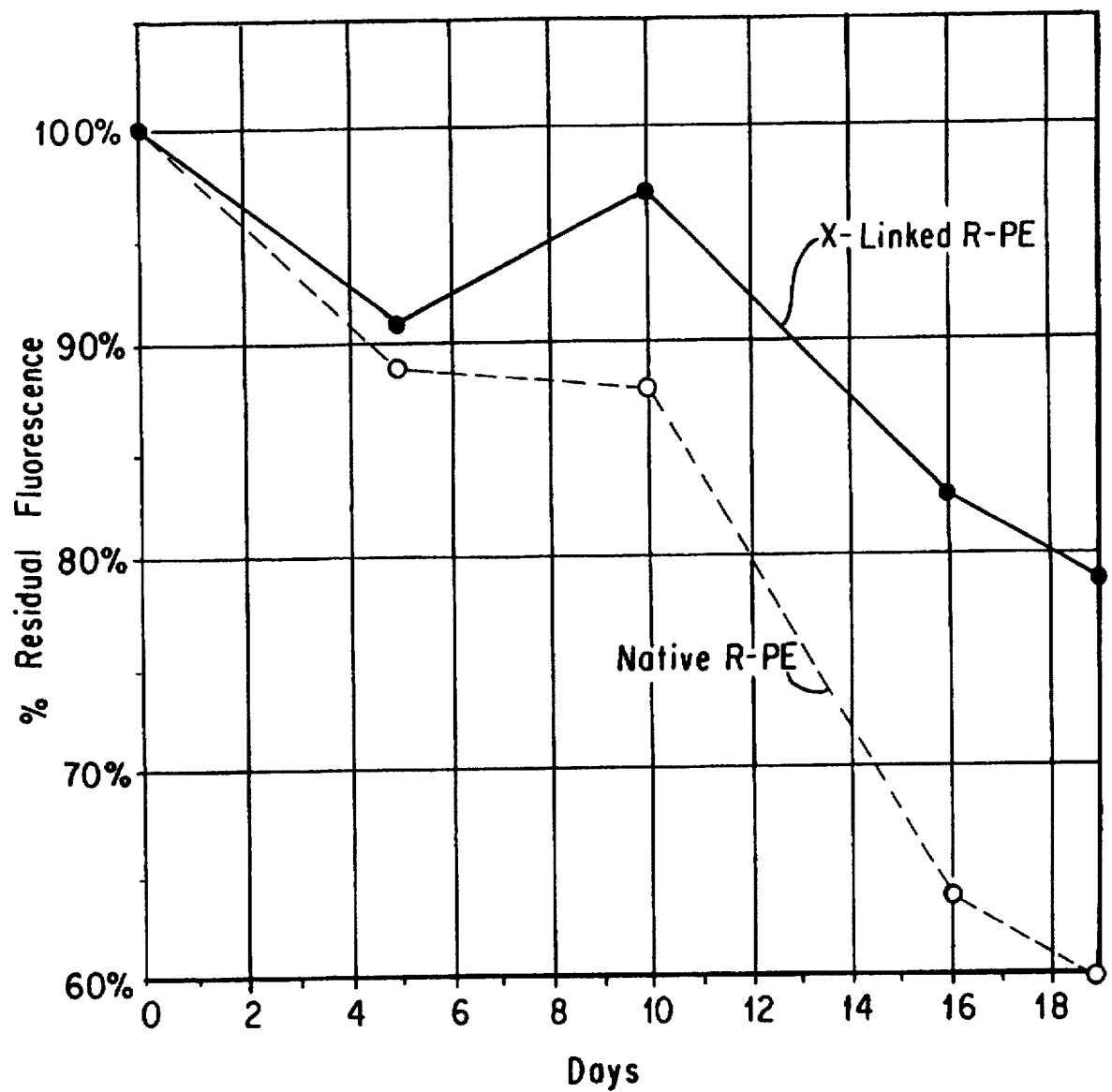

The thermal stability of poly(glutamic acid) poly (phosphorothioate) crosslinked R-PE was evaluated at 45° C. and compared to native R-PE under the same conditions. Both the native protein and the crosslinked protein were diluted to 100 µg/ml with buffer E. These dilutions were stored in a 45° C. incubator for the duration of the study. At day 0 and various time points along the course of the study the fluorescence intensity of both preparations was evaluated. Prior to evaluation, the stressed protein preparations were diluted to 1 µg/ml using buffer E. Fluorescence intensity measurements were performed using an F-4010 fluorescence spectrophotometer. The fluorescence by the R-PE preparations at the various time points was divided by the fluorescence by the same preparation at day 0 to calculate the percent residual fluorescence intensity for the stressed preparations. The results of this evaluation are shown in FIG. 12.

(d) Thermal Stability Evaluation of Crosslinked R-PE by Size

Figure 13:
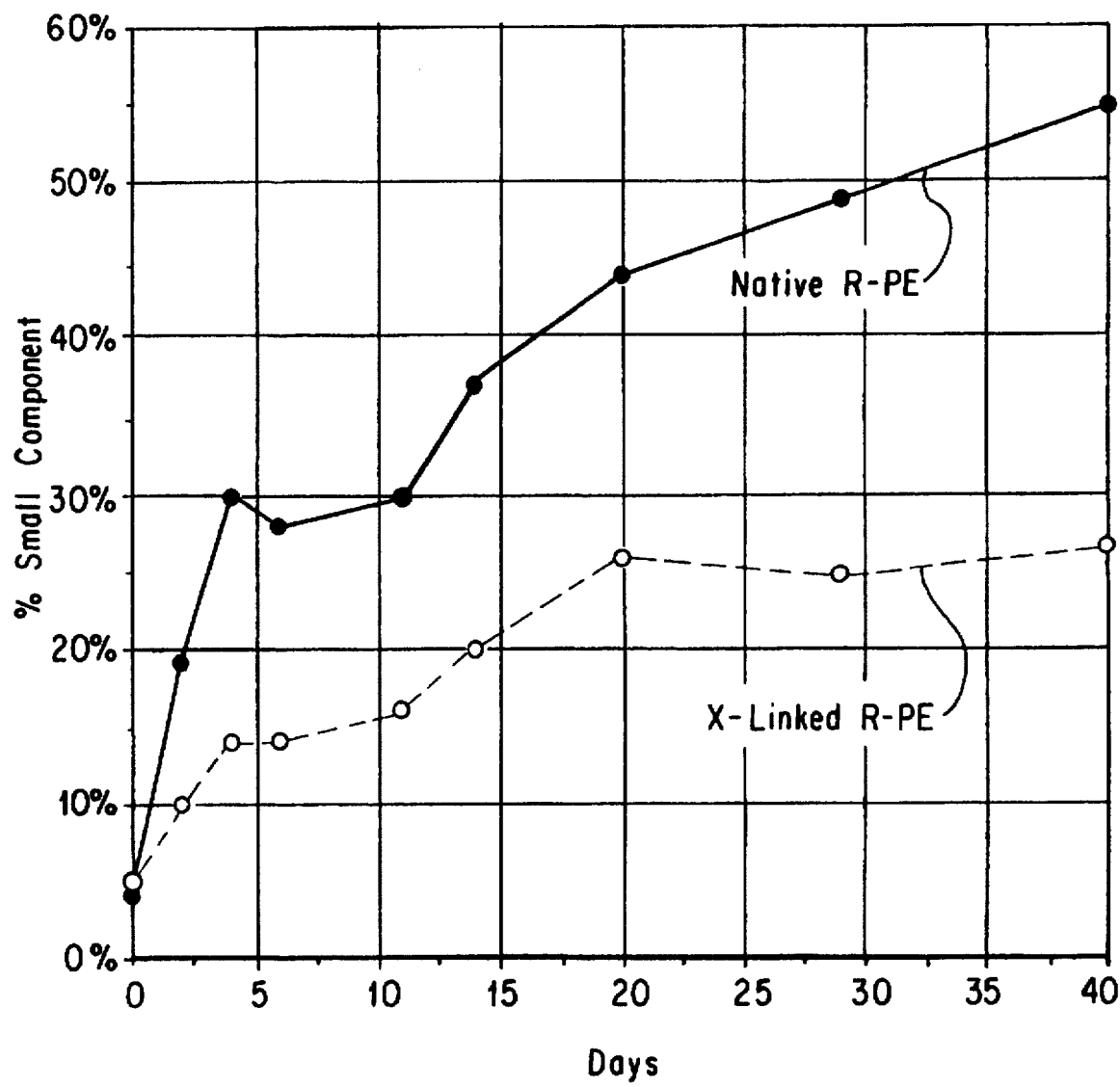

The thermal stability of poly(glutamic acid) poly (phosphorothioate) crosslinked R-PE was evaluated at 45° C. and compared to native R-PE under the same conditions. A Bio-Sil SEC-400 column was used to follow the decomposition of the stressed R-PE into smaller subunit components. Detection was at 280 nm. The mobile phase was buffer E running at a flow rate of 1.0 ml/minute. Both the native protein and the crosslinked protein were diluted to 100 µg/ml with buffer E. These dilutions were stored in a 45° C. incubator for the duration of the study. At day 0 and various time points along the course of the study the percentage of the total 280 nm absorbance which was due to the small components was evaluated. The results of this evaluation are shown in FIG. 13.

EXAMPLE 6

Poly(glutamic acid) Poly(phosphorothioate) Crosslinked

Bovine Alkaline Phosphatase (ALP)/Anti-TSH IgG Conjugate (a) Derivatization of Anti-TSH Antibody To 1 ml of 6.6 mg/ml anti-TSH IgG was added 1 ml of buffer C. The antibody was concentrated to approximately 0.2 ml using a Centricon-30-Concentrator with a MW cutoff of 30,000. The concentrate was rediluted to 2 ml using buffer C, then reconcentrated to 0.2 ml. This concentration/dilution procedure was repeated three times. The volume of the antibody solution was made up to 1 ml with buffer C and placed in a vial. To 50 µl of DMF was added 0.56 mg (831 nmol) of succinimidyl (tricaproamido cyclohexylmethyl) N-maleimide (STCM) linker. The linker was prepared as described in U.S. Pat. No. 4,994,385 which is herein incorporated by reference. This solution was added to 0.47 ml of 5.30 mg/ml (16.6 nmol) washed antibody and allowed to react for one hour at room temperature while rotating at 100 rpm on a rotary agitator. A Sephadex G-25 was prepared as above with buffer C and following the incubation, the derivatized antibody was applied to the G-25 column to remove unreacted linker. The column was eluted with buffer C and 0.75 ml fractions were collected. Fractions with an $A_{280}$ greater than 0.5 AU were pooled and the $A_{280}$ of the pool used to calculate the concentration of the linker derivatized antibody. The antibody pool was stored on ice until conjugated.

(b) Conjugation of Linker Derivatized Anti-TSH IgG to Poly(glutamic acid) Poly(phosphorothioate) Crosslinked ALP To a 0.72 ml aliquot of 0.83 mg/ml (4 nmol) linker derivatized anti-TSH IgG was added 0.69 ml of 1.30 mg/ml (6 nmol) poly(glutamic acid) poly(phosphorothioate) crosslinked ALP (prepared in accordance with Example 2). The resulting mixture was allowed to react overnight at 5° C. while rotating at 100 rpm on a rotary agitator.

EXAMPLE 7

Poly(glutamic acid) Poly(phosphorothioate) Crosslinked R-phycoerythrin (R-PE)/anti-CD8 IgG Conjugate (a) Derivatization of Anti-CD8 Antibody.

To 1 ml of 4.1 mg/ml anti-CD8 IgG was added 1 ml of buffer E. The antibody was concentrated to approximately 0.2 ml using a Centricon-30-Concentrator with a MW cutoff of 30,000. The concentrate was rediluted to 2 ml using buffer E then reconcentrated to 0.2 ml. This concentration/dilution procedure was repeated three times. The volume of the antibody solution was made up to 1 ml with buffer E and placed in a vial. To 150 µl of DMF was added 0.15 mg (223 nmol) of STCM linker (as prepared in example 6). This solution was added to 0.50 ml of 4.39 mg/ml (14.6 nmol) washed antibody and allowed to react for one hour at room temperature while rotating at 100 rpm on a rotary agitator. A Sephadex G-25 column was prepared as above with buffer E and following the incubation, the derivatized antibody was applied to the G-25 column to remove unreacted linker. The column was eluted with buffer E and 0.75 ml fractions were collected. Fractions with an $A_{280}$ greater than 0.5 AU were pooled and the $A_{280}$ of the pool used to calculate the concentration of the linker derivatized antibody. The antibody pool was stored on ice until conjugated.

(b) Conjugation of Linker Derivatized Anti-CD8 IgG to Poly(glutamic acid) Poly(phosphorothioate) Crosslinked R-PE To a 0.53 ml aliquot of 1.71 mg/ml (6 nmol) linker derivatized anti-CD8 IgG was added 0.68 ml of 2.11 mg/ml (6 nmol) poly(glutamic acid) poly(phosphorothioate) crosslinked R-PE (prepared in accordance with Example 5). The resulting mixture was allowed to react overnight at 5° C. while rotating at 100 rpm on a rotary agitator.

EXAMPLE 8

Preparation of Goat Anti-alpha hCG Antibody/ Bovine Alkaline Phosphatase (ALP) Conjugate Using Poly(glutamic acid) Poly (phosphorothioate) as a Template (a) Derivatization of Goat Anti-Alpha hCG Antibody A 1 ml aliquot of goat anti-alpha hCG antibody containing 2.8 mg (18.7 nmol) was diluted with 1 ml buffer E. The antibody was concentrated to approximately 0.2 ml by centrifugation at 5000×g using a Centricon-30-Concentrator which contains a membrane sized to pass material having a number average molecular weight of up to about 30,000. The concentrate was diluted to 2 ml with buffer E and reconcentrated to approximately 0.2 ml. This concentration and dilution procedure was repeated two more times. Next, the volume was made up to 1 ml with buffer E and the antibody solution was placed into a vial. To the antibody solution was added 0.19 mg (280 nmol) of STCM linker (prepared as in Example 6) dissolved in 100 µl of DMF. The resulting reaction mixture was gently stirred on a rotary agitator for one hour at ambient temperature. The derivatized antibody was purified by size exclusion chromatography using a 1×45 cm column of Sephadex G-25. The column was equilibrated and eluted with buffer E. Fractions of about 1 ml each were collected during elution and the absorbance at 280 nm was determined. The peak fractions were pooled and the concentration of the antibody in the pool was calculated from its absorbance at 280 nm using an extinction coefficient (E1cm1%) of 13.9. The antibody pool was stored on ice until conjugation.

(b) Derivatization of ALP

A 0.7 ml aliquot containing 7 mg (46.6 nmol) ALP was diluted to 2 ml with buffer C, and concentrated to approximately 0.2 ml by centrifuging at 5000×g using a Centricon-30-Concentrator. The concentrated enzyme was diluted again to 2 ml with buffer C and reconcentrated to about 0.2 ml. The volume was made up to 1 ml with buffer C and the enzyme solution was placed into a vial. To the enzyme solution was added 0.63 mg (935 nmole) of STCM (prepared as in Example 6) dissolved in 200 µl of DMF. The resulting reaction mixture was gently stirred on a rotary agitator for 30 minutes at ambient temperature and the derivatized enzyme was purified by size exclusion chromatography using a 1×45 cm column of Sephadex G-25. The column was equilibrated and eluted with buffer C. Fractions of about 1 ml each were collected during elution and the absorbance at 280 nm was determined. The peak fractions were pooled and the concentration of the enzyme in the pool was calculated from its absorbance at 280 nm using an extinction coefficient (E1cm1%) of 10.

(c) Conjugation of Derivatized Enzyme and Antibody with Poly(Glutamic Acid) Poly(Phosphorothioate) as a Template Three conjugates were prepared, with varying molar ratios of antibody:enzyme:poly(glutamic acid) poly (phosphorothioate), as follows:

Conjugate 1:

Antibody:Enzyme:Poly(Glutamic Acid) Poly (Phosphorothioate) (1:1:1)

1.0 ml aliquot (0.7 mg or 4.6 nmol) of the derivatized anti-alpha hCG antibody was mixed with 0.45 ml (0.7 mg or 4.7 nmol) of the derivatized ALP, and 0.32 ml (0.32 mg or 4.6 nmol) of an aqueous solution of poly(glutamic acid) poly(phosphorothioate). The resulting mixture was gently stirred on a rotary agitator overnight at 2°–8° C.

Conjugate 2:

Antibody:Enzyne:Poly(Glutamic Acid) Poly (Phosphorothioate) (1:3:1)

0.68 ml (0.5 mg or 3.3 nmol) of the solution of derivatized anti-alpha hCG antibody, was mixed with 0.96 ml (1.5 mg or 10 nmol) of the derivatized ALP, and 0.23 ml (0.23 mg or 3.3 nmol) of an aqueous solution of poly(glutamic acid) poly(phosphorothioate). The resulting mixture was gently stirred on a rotary agitator overnight at 2°–8° C.

Conjugate 3:

Antibody:Enzyme:Poly(Glutamic Acid) Poly (Phosphorothioate) (1:1:0.5)

1.0 ml (0.7 mg or 4.6 nmol) of the solution of derivatized anti-alpha hCG antibody was mixed with 0.45 ml (0.7 mg or 4.6 nmol) of the derivatized ALP and 0.17 ml (0.17 mg or 2.4 nmol) of an aqueous solution of poly(glutamic acid) poly(phosphorothioate). The resulting mixture was gently stirred on a rotary agitator overnight at 2°–8° C.

All three conjugates were evaluated by size exclusion HPLC. No residual antibody or enzyme were detected in conjugates 1 and 3. Conjugate 2, however, contained about 20% residual starting material, presumably enzyme.

The unreacted thiol groups on conjugated or any free poly(glutamic acid) poly(phosphorothioate) were capped by treatment with N-ethylmaleimide (NEM) for a period of 1 hour at ambient temperature. Aliquots of a 5 mM solution were added to the conjugate so that the final concentration of NEM in the conjugate was about 0.3 mM.

EXAMPLE 9

Preparation of Anti-pancreatic Thread Protein Antibody/Bovine Alkaline

Phosphatase (ALP) Conjugate Using Poly(glutamic acid)

Poly(phosphorothioate) as a Template (a) Derivatization of Anti-Pancreatic Thread Protein Antibody 4.0 ml of 1 mg/ml solution of anti-pancreatic thread protein antibody was concentrated to approximately 0.2 ml by centrifuging at 5000×g using a Centricon-30-Concentrator and the concentrate was diluted to 2 ml with the buffer E and reconcentrated to approximately 0.2 ml. The concentration and dilution procedure was repeated two more times after which the volume was made up to 1 ml with buffer E. The antibody solution was placed into a vial and 0.27 mg of STCM linker (prepared as in Example 6) dissolved in 100 µl of DMF was added. The resulting reaction mixture was gently stirred on a rotary agitator for one hour at ambient temperature. The derivatized antibody was purified by chromatography on a 1×45 cm column of Sephadex G-25. The column was equilibrated and eluted with buffer E. Fractions of about 1 ml each were collected during elution and the absorbance at 280 nm was determined.

The peak fractions were pooled and the concentration of the antibody in the pool was calculated from its absorbance at 280 nm using an extinction coefficient (E1cm1%) of 13.9. The antibody pool was stored on ice until used in the conjugation reaction.

(b) Derivatization of ALP

A 0.7 ml aliquot of 10 mg/ml (46.6 nmole) ALP was diluted to 2 ml with buffer C and concentrated to approximately 0.2 ml by centrifuging at 5000×g using a Centricon-30-Concentrator. The concentrated enzyme was diluted again to 2 ml and reconcentrated to about 0.2 ml. The volume was made up to 1 ml with buffer C and the enzyme solution was placed into a vial. To the enzyme solution was added 0.63 mg (935 nmol) of STCM (prepared as in Example 6) dissolved in 200 µl of DMF. The resulting reaction mixture was gently stirred on a rotary agitator for 30 minutes at ambient temperature and the derivatized enzyme was purified by chromatography on a 1×45 cm column of Sephadex G-25. The column was equilibrated and eluted with buffer C. Fractions of about 1 ml each were collected during elution and the absorbance at 280 nm was determined. The peak fractions were pooled and the concentration of the enzyme in the pool was calculated from its absorbance at 280 nm using an extinction coefficient (E1cm1%) of 10.

(c) Conjugation of Derivatized Enzyme and Antibody with Poly(Glutamic Acid) Poly(Phosphorothioate) as a Template Two conjugates were prepared, with varying molar ratios of antibody:enzyme:poly(glutamic acid)poly (phosphorothioate), as follows:

Conjugate 1:

Antibody:Enzyme:Poly(Glutamic Acid) Poly (Phosphorothioate) (1:1:1)

1.25 ml (0.7 mg or 4.7 nmol) of the derivatized anti-pancreatic thread protein antibody was mixed with 0.45 ml (0.7 mg or 4.7) of the derivatized ALP, and 0.32 ml (0.32 mg or 4.6 nmol) of an aqueous solution of poly(glutamic acid) poly(phosphorothioate). The resulting mixture was gently stirred on a rotary agitator overnight at 2°–8° C.

Conjugate 2:

Antibody:Enzyme:Poly(Glutamic Acid) Poly (Phosphorothioate) (1:3:1)

0.89 ml (0.5 mg or 3.3 nmol) of the solution of derivatized anti-pancreatic thread protein antibody was mixed with 0.96 ml (1.5 mg or 10 nmol) of the derivatized ALP and 0.23 ml (0.23 mg or 3.3 nmol) of an aqueous solution of poly (glutamic acid) poly(phosphorothioate). The resulting mixture was gently stirred on a rotary agitator overnight at 2°–8° C.

The two conjugates were evaluated by size exclusion HPLC. No residual antibody or enzyme were detected in conjugates 1. Conjugate 2, however, contained about 20% residual starting material, presumably enzyme.

The unreacted thiol groups on conjugated or any free poly(glutamic acid) poly(phosphorothioate) were capped by treatment with NEM for a period of 1 hour at ambient temperature as mentioned in Example 8c.

EXAMPLE 10

Acid Deprotection of Cysteamine-S-phosphate

Three 5 µl aliquots of 8.2 mM aqueous solution of cysteamine-S-phosphate were placed into three separate vials. The three samples were diluted to 1 ml with 0.1M sodium acetate buffer, pH 4.0. The final pH of the samples was found to be 4.0. The samples were left at ambient temperature and neutralized either at 1, 3, or 19 hours by addition of 50 μl of approximately 5M sodium hydroxide and 2 ml of 0.1M sodium phosphate, pH 8.5. The thiol groups generated were quantified colorimetrically after addition of 20 μl of 10 mM solution of DTNB. The absorbance was read within 5 minutes of the addition of DTNB at 412 nm against a reagent blank with no cysteamine-S-phosphate. The experimentally determined molar extinction coefficient of 13,000 was used in thiol quantification. The results are summarized below in Table 2.

The experiment was repeated exactly as described above but with three times higher concentration of cysteamine-S-phosphate. For controls, same amounts of cysteamine-S-phosphate were taken up in 0.1M sodium phosphate buffer, pH 7.0, and subjected to thiol quantification after appropriate intervals. The results are summarized below in Table 3.

TABLE 2

|  | Cysteamine-S-Phosphate pH 4.0 Exposure | | |
| --- | --- | --- | --- |
|  | 1 hour | 3 hours | 19 hours |
| Thiols Generated (nmol) | 8.2 | 19.2 | 29.3 |
| % Thiol Deprotection | 20 | 46.8 | 71.5 |

TABLE 3

|  | Cysteamine-S-Phosphate pH 4.0 Exposure | | |
| --- | --- | --- | --- |
|  | 1 hour | 3 hours | 19 hours |
| Thiols Generated (nmol) | 32.8 | 51.6 | 77.5 |
| % Thiol Deprotection | 26.7 | 42.0 | 63.0 |

The extent of acid catalyzed deprotection was found to be time dependent. A nineteen hour incubation resulted in 63 to 71.5% deprotection of the thiophosphate groups.

EXAMPLE 11

Immobilization of Anti-TSH Antibody to Amino Microparticles (a) Functionalization of the Antibody An aliquot of anti-TSH antibody containing 5 mg (33 nmol) is extensively dialyzed against buffer E and placed in a vial. To the antibody solution is added 0.22 mg (660 nmol) of SMCC dissolved in 100 μl of DMF and the resulting mixture is gently stirred for 30 minutes at ambient temperature. The activated antibody is recovered by chromatography over a 1×45 cm column of Sephadex G-25. The column is equilibrated and eluted with buffer E. Fractions of about 1 ml each are collected during elution and absorbance at 280 nm is determined. The peak fractions are pooled and the concentration of the antibody in the pool is calculated from its absorbance at 280 nm using an extinction coefficient (E1cm1%) of 13.9.

To the activated antibody pool (4 mg or 26.7 nmol) is added 20 μl (0.2 mg or 1.3 nmol) of a solution of ALP and 8 mg (133 nmol) of poly(glutamic acid) poly (phosphorothioate) (MW=60,000; 25 phosphorothioate groups/poly(glutamic acid) poly(phosphorothioate) dissolved in 0.8 ml of buffer E. The resulting mixture is gently stirred overnight at 2°–8° C. The poly(glutamic acid) poly (phosphorothioate) functionalized antibody is stored on ice until coupling to microparticles.

(b) Activation of Amino Microparticles One milliliter of amino microparticles (diameter=0.25 μm, % solids=10) is suspended in 3 ml of distilled water followed by addition of 2 g of the anion exchange resin, BIO-REX MSZ 501(D). The resin/microparticle mixture is rotated end over end for 1 hour at ambient temperature and then poured into a course sintered glass funnel. The microparticles are pulled through the funnel under low vacuum and centrifuged at 18,000 rpm for 30 minutes. The supernatant is decanted carefully and the microparticles are washed with 10 ml of water, and centrifuged. The supernatant is decanted and the washed microparticles are suspended in 4 ml of buffer E. 8 mg of STCM (prepared in accordance with Example 6) is dissolved in 4 ml of DMF and added to the microparticle suspension. The mixture is rotated end over end for one hour at ambient temperature and then poured into a centrifuge tube. Buffer E is added to final volume of 32 ml and the microparticles are centrifuged at 15,000 rpm for 30 minutes. The supernatant is decanted and microparticles are resuspended in 30 ml of buffer E. The washing with buffer E is repeated two more times and the washed microparticles are finally resuspended in 4 ml of buffer E.

(c) Coupling of Antibody to Microparticles

The poly(glutamic acid) poly(phosphorothioate) functionalized antibody pool (3 ml containing 4 mg) is combined with the activated microparticles and the resulting suspension is rotated end over end overnight at 2°–8° C. The microparticles are poured into a centrifuge tube and buffer E containing 1 mg/ml bovine serum albumin (BSA) is added to 35 ml. The microparticles are centrifuged and resuspended in 35 ml buffer E containing BSA, after the supernatant has been decanted. The particles are washed two more times to ensure removal of any free antibody and then resuspended in an appropriate storage buffer and stored at 2°–8° C.

EXAMPLE 12

Poly(glutamic acid) poly(phosphorothioate) Crosslinked Bovine Alkaline

Phosphatase (ALP) Site-Specifically Conjugated with Anti-Hepatitis B Surface

Antigen IgG (a) Derivatization of Anti-hepatitis B Surface Antigen (HBsAg) Antibody To 10 ml of 1.1 mg/ml anti-Hepatitis B surface antigen IgG was added 10 ml of 0.1M triethanolamine (TEA), 0.16M NaCl, pH 8.0 buffer (buffer I).

The antibody was concentrated to approximately 1.5 ml using a Centriprep-30-Concentrator with a MW cutoff of 30,000. The concentrate was rediluted to 20 ml using buffer I then reconstituted to 1.5 ml. This concentration/dilution procedure was repeated three times. The volume of the final concentrated antibody solution was diluted to 2 ml with buffer I and placed in an amber vial. To 1.71 ml of the 4.68 mg/ml (53.3 nmol) washed IgG was added 160 μl of 200 mM (320 nmol) sodium m-periodate dissolved in buffer I. This mixture was allowed to react for one hour at room temperature while rotating on a rotary agitator. Following the incubation, the above reaction mixture, which contained oxidized antibody, was applied to the equilibrated G-25 column which had been prepared as above using buffer E. The column was eluted with buffer E and 0.75 ml fractions were collected. Fractions with an $A_{280}$ greater than 0.3 AU were pooled. The antibody pool was concentrated to 1 ml using a Centricon-30-Concentrator with a MW cutoff of 30,000. To the concentrated antibody pool was added 250 μl of 0.75M (188 μgmol) cystamine dihydrochloride dissolved in buffer E. Following a 15 minute incubation at room temperature with gentle stirring, 63 µl of 0.3M (18.9 µmol) sodium cyanoborohydride dissolved in buffer E was added and the resulting mixture was allowed to react at room temperature overnight After the overnight incubation, the reaction mixture was applied to a Sephadex G-25 column that had been prepared as above using 0.1 M sodium phosphate, 0.1M NaCl, 2 mM EDTA, pH 7.0 buffer (buffer J). The column was eluted with buffer J and 0.75 ml fractions were collected. Fractions with an $A_{280}$ greater than 0.3 AU were pooled. The antibody pool was concentrated to 1.5 ml using a Centricon-30-Concentrator with a MW cutoff of 30,000. To the concentrated antibody pool was added 75 µl of 40 mM (30 nmol) DTT dissolved in buffer J. This mixture was allowed to react for 15 minutes at room temperature while rotating at 100 rpm on a rotary agitator. After the reaction, the mixture was applied to a Sephadex G-25 column that had been prepared as above using buffer J. The column was eluted with buffer J and 0.75 ml fractions were collected. Fractions with an $A_{280}$ greater than 0.3 AU were pooled. The resulting Fc-functionalized antibody with free thiols in the Fc region was stored on ice until conjugated.

(b) Derivatization of Poly(glutamic acid) Poly (phosphorothioate) Crosslinked ALP To a 2.27 ml aliquot of 2.64 mg/ml (40 nmol) poly (glutamic acid) poly (phosphorothioate) crosslinked ALP (prepared in accordance with Example 2) was added 100 µl of 0.16M NEM (16 µmol). The resulting mixture was allowed to incubate for one hour while rotating at 100 rpm on a rotary agitator. To 50 µl of DMF was added 0.54 mg (831 nmol) of STCM linker which was prepared as described in Example 6. This linker solution was added to 1.18 ml of 2.53 mg/ml (20 nmol) NEM capped crosslinked ALP and allowed to react for one hour at room temperature while rotating at 100 rpm on a rotary agitator.

After the reaction was complete, the mixture was applied to a Sephadex G-25 column which had been prepared as above except that the column was equilibrated with three column volumes buffer C. The column was eluted with buffer C and 0.75 ml fractions were collected. Fractions with an $A_{280}$ greater than 0.3 AU were pooled. The linker functionalized crosslinked ALP was stored on ice until conjugated.

(c) Conjugation of Fc Derivatized Anti-hepatitis B Surface Antigen IgG to Poly(glutamic acid) Poly(phosphorothioate) Crosslinked ALP To a 0.52 ml aliquot of 0.97 mg/ml (3.5 nmol) Fc derivatized anti-Hepatitis B surface antigen IgG was added 1.30 ml of 0.77 mg/ml (7 nmol) STCM linker derivatized NEM capped poly(glutamic acid) poly(phosphorothioate) crosslinked ALP. The resulting mixture was allowed to react overnight at 5° C. while rotating at 100 rpm on a rotary agitator to yield the conjugated product.

EXAMPLE 13

Poly(glutamic acid) Poly(phosphorothioate) Crosslinked Bovine Alkaline

Phosphatase (ALP)/Fc Site-Specifically Derivatized Anti-hCG IgG Conjugate (a) Derivatization of Anti-hCG Antibody.

To 8 ml of 1.1 mg/ml anti-hCG IgG was added 10 ml of buffer I and the antibody was concentrated to approximately 1.5 ml using a Centriprep-30-Concentrator. The concentrate was rediluted to 20 ml using buffer I then reconcentrated to 1.5 ml. This concentration/dilution procedure was repeated three times. The volume of the antibody solution was made up to 2 ml with buffer I and placed in an amber vial. To 2 ml of 4.0 mg/ml (53.3 nmol) washed IgG was added 220 ml of 200 mM (440 nmol) sodium m-periodate dissolved in buffer I. This mixture was allowed to react for one hour at room temperature while rotating at 100 rpm on a rotary agitator. Following the incubation, the above reaction mixture, which contained the oxidized antibody, was applied to a G-25 column as prepared above using buffer E. The column was eluted with buffer E and 0.75 ml fractions were collected. Fractions with an $A_{280}$ greater than 0.3 AU were pooled. The antibody pool was concentrated to 1 ml using an Amicon Centricon-30-Concentrator. To the concentrated antibody pool was added 300 ml of 15 mM (4.81 mmol) 4-(N-maleimidomethyl) cyclohexane-1-carboxyl hydrazide ($M_2C_2H$) linker dissolved in buffer E. This mixture was allowed to react for three hours at room temperature while rotating at 100 rpm on a rotary agitator. Following the incubation, the above reaction mixture was applied to a G-25 column as prepared above except 0.1M sodium acetate, 0.1M NaCl, pH 6.0 (buffer K) was employed to remove unreacted linker. The column was eluted with buffer K and 0.75 ml fractions were collected. Fractions with an $A_{280}$ greater than 0.3 AU were pooled. The Fc-functionalized antibody with maleimides in the Fc region was stored on ice until conjugated.

(b) Conjugation of Fc Derivatized Anti-hCG IgG to Poly (glutamic acid) Poly(phosphorothioate) Crosslinked ALP To a 1 ml aliquot of 2 mg/ml (13.3 nmol) Fc derivatized anti-hCG IgG is added 1 ml of 4 mg/ml (26.6 nmol) poly(glutamic acid) poly(phosphorothioate) crosslinked ALP (prepared in accordance with the technique described in Example 2). The resulting mixture is allowed to react overnight at 5° C. while rotating at 100 rpm on a rotary agitator to yield the conjugated product.

EXAMPLE 14

Synthesis of Dithiothreitol Diphosphate

A solution of 1,4-dibromo-2,3-butanediol (1.0 g, 4.0 mmol) in 5 ml DMF is added to sodium thiophosphate dodecahydrate (3.8 gm, 10.1 mmol) in 20 ml $H_2O$. The mixture is stirred overnight at room temperature. A 5% silver nitrate solution is added to precipitate excess sodium thiophosphate. The precipitate is filtered out and the filtrate dried under high vacuum. The solid residue is triturated with methanol and filtered to yield 1.8 g (3.8 mmol) of threitol bis-phosphorothioate tetrahydrate.

EXAMPLE 15

Dithiothreitol Diphosphate Deprotection

When phosphorothioate deprotection of the bisphosphorothioate threitol is desired, to activate its reducing ability, the cleavage of the phosphate bonds is accomplished by addition of 1 µM solution of ALP. Due to the chelating nature of dithiothreitol, zinc and magnesium are added to the reaction medium to maintain the catalytic activity of the ALP.

EXAMPLE 16

Synthesis of Phosphorothioate Heterobifunctional Agents (a) N-hydroxysuccinimidyl Cysteamidophosphorothioate 4,5-Dithioheptyl 1-Carboxylate 48.2 mg (269 µmol) of cysteamine-S-phosphate was dissolved in 2.5 ml of deionized water and the resulting solution was added to a solution of 330 mg (816 µmol) of 3,3'-dithiopropionic acid bis-active ester in 2.5 ml of DMF. The two solutions were combined while stirring at room temperature and the stirring was continued for an additional 3 minutes after the solutions were combined. After the 3 minute mixing period the solution was evaporated under reduced pressure for 18 minutes at room temperature. 20 ml of chloroform was added to the resulting white residue and the mixture was stirred for 10 minutes. A white precipitate formed which was separated from the supernatant liquid and dried under reduced pressure to yield the powder product N-hydroxysuccinimidyl cysteamidophosphorothioate 4,5-dithioheptyl 1-carboxylate.

FAB(−) mass spectrum data indicated the presence of material of m/e −1=445, the expected m/e of the desired product is 446. FAB (+) spectrum data also indicated the presence of the appropriate ion (m/e+ Na+).

20 (b) N-hydroxysuccinimidyl Cysteamidophosphorothioate 3-Oxybutyl 1-Carboxylate 50 mg (279 μmol) of cysteamine-S-phosphate was dissolved in deionized water and the resulting solution was added to a solution of 370 mg (1.12 μmol) of diglycolic acid bis-active ester dissolved in DMF. The solutions were mixed at room temperature during the addition and the stirring was continued for an additional 3 minutes after the addition was complete. After the stirring period was complete, the reaction mixture was evaporated under reduced pressure at room temperature for 20 minutes. 35 ml of tetrahydrofuran (THF) was added to the resulting white residue and the resulting mixture was stirred for 10 minutes. A white precipitate formed and was separated from the supernatant liquid and dried under reduced pressure to yield the product N-hydroxysuccinimidyl cysteamidophosphorothioate 3-oxybutyl 1-carboxylate as a white powder.

FAB(−) mass spectrum data indicated the presence of material of m/e −1=369, the expected m/e of the desired product is 370. FAB (+) spectrum data also indicated the presence of the appropriate ion (m/e+ Na+) however, the presence of large amounts of sodium ions produced a strong background.

(c) N-hydroxysuccinimidyl Cysteamidophosphorothioate Heptanoyl 1-Carboxylate 50 mg (279 μmol) of cysteamine-S-phosphate sodium salt was dissolved in 3 ml of deionized water and added to a solution of 400 mg (1.086 μmol) of the bis-active ester of suberic acid dissolved in 3 ml of DMF. The addition was performed over the course of 1 minute at 5° C. The resulting reaction mixture was stirred at room temperature for 1 hour and 45 minutes. The reaction mixture was then evaporated to dryness under reduced pressure at room temperature for 18 minutes and the resulting solid residue was treated with 10 ml of THF. A white precipitate formed and was collected and treated again with 10 ml of THF. A white precipitate was again collected and dried under reduced pressure to yield the product N-hydroxysuccinimidyl cysteamidophosphorothioate heptanoyl 1-carboxylate.

FAB(−) mass spectrometry indicated the presence of the molecular ion m/e−1=409 which corresponds to the m/e of the desired material of m/e=410.

(d) Cysteamidophosphorothioate Heptanoyl 1-Hydrazide 0.10 gm (250 μmol) of N-hydroxysuccinimidyl cysteamidophosphorothioate heptanoyl 1-carboxylate is dissolved in 2 ml of a 1:1 solution of DMF in deionized water and the resulting solution is added to a solution of 1 mmol of hydrazine monohydrate dissolved in 2 ml of a 1:1 solution of DMF in deionized water. The resulting reaction mixture is incubated while stirring for 10 minutes at 0° C. After the incubation the reaction mixture is evaporated until dry under reduced pressure. The solid residue is then washed three times with 10 ml of THF per wash. Precipitate formed after the last wash is then dried under reduced pressure.

(e) Cysteamidophosphorothioate Heptanoyl 1-(Aminoethyl) carboxamide 0.1 gm (250 μmol) of N-hydroxysuccinimidyl cysteamidophosphorothioate heptanoyl 1-carboxylate is dissolved in a 1:1 solution of DMF in deionized water and the resulting solution is added to a solution of 1 mmol of ethylenediamine dissolved in 2 ml of a 1:1 solution of DMF in deionized water. The resulting reaction mixture is incubated while stirring for 10 minutes at 0° C. After the incubation the reaction mixture is evaporated until dry under reduced pressure. The solid residue is then washed three times with 10 ml of THF per wash. Precipitate formed after the last wash is then dried under reduced pressure.

(f) p-Nitrophenyl Cysteamidophosphorothioate Heptanoyl 1-Carboxylate 250 μmol of N-hydroxysuccinimidyl cysteamidophosphorothioate heptanoyl 1-carboxylate [from Example 16(c)] is dissolved in 3 ml of deionized water. 1 mmol of p-nitrophenol is dissolved in 3 ml of DMF and added to the N-hydroxysuccinimidyl cysteamidophosphorothioate heptanoyl 1-carboxylate solution. The resulting reaction mixture is stirred at room temperature for 2 hours and then evaporated until dry under reduced pressure. The solid residue is then washed three times with 10 ml of THF per wash. Precipitate formed after the last wash is then dried under reduced pressure.

EXAMPLE 17

Stoichiometric Control of the Size of Poly(glutamic acid)

Poly(phosphorothioate) Crosslinked Bovine Alkaline Phosphatase (ALP)

(a) Preparation of Poly(glutamic acid) Poly (phosphorothioate) Crosslinked ALP

A number of poly(glutamic acid) poly(phosphorothioate) crosslinked ALP preparations were produced over a range of poly(glutamic acid) poly(phosphorothioate) to ALP ratios. Using the crosslinking techniques set forth in Example 2, poly(glutamic acid) poly(phosphorothioate)to ALP ratios of 1:1, 2:1, 3:1, 4:1, and 6:1 were employed to crosslink ALP. The products of the crosslinking reactions were evaluated in order to determine the effect of varying the molar ratio of reactants had on controlling the size of the crosslinked ALP.

b) Characterization of Crosslinked ALP

Poly(glutamic acid) poly(phosphorothioate) crosslinked ALP was evaluated by size exclusion chromatography using a Bio-Sil SEC-400 column. Detection was at 280 nm. The mobile phase was buffer E running at a flow rate of 1.0 ml/minute. From the HPLC chromatograms, the percentage of product with a retention time corresponding to singlet crosslinked ALP was calculated.

Figure 15:
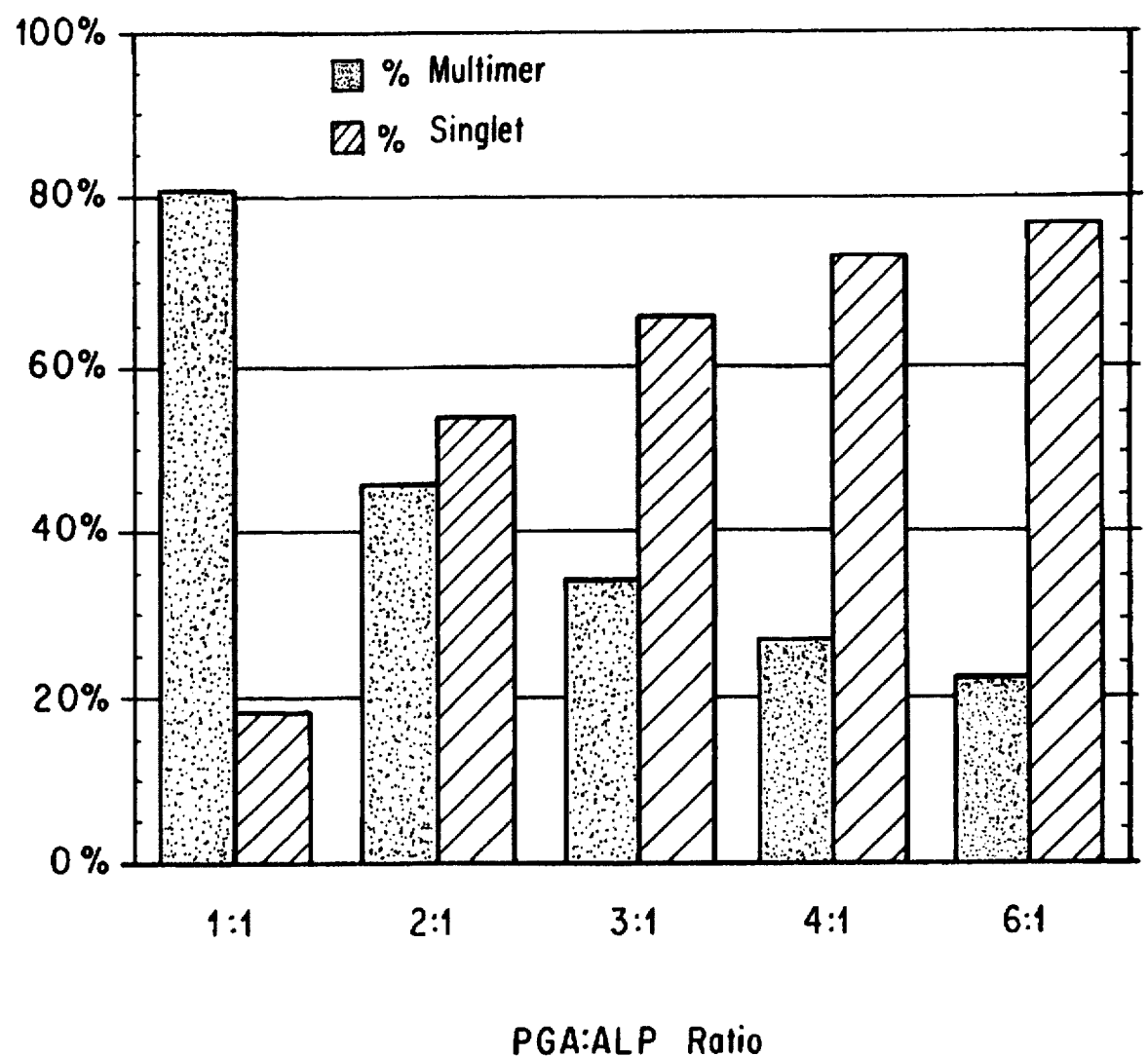
FIG. 15 illustrates the effect stoichiometric manipulation has on the size of the products produced in crosslinking reaction.

The results of this evaluation are shown in FIG. 15. As shown by FIG. 15, the amount of monomeric crosslinked ALP produced per crosslinking reaction increased as a function of increasing the amount of poly(glutamic acid) poly(phosphorothioate). Additionally, the amount of multimers produced decreased when the amount poly(glutamic acid) poly(phosphorothioate) was increased. Hence, through stoichiometric manipulation, modulation of the size of the crosslinked ALP was possible.

While the invention has been described in detail and with reference to specific embodiments thereof, it will be apparent to one skilled in the art that various changes and modifications may be made therein without departing from the spirit and scope thereof. Additionally, all references to patents or publications in this specification are incorporated herein by reference.

What is claimed is:

1. A method of conjugating compounds comprising the steps of:

(a) activating a conjugating agent by deprotecting a thiol group of a phosphorothioate monoester of said conjugating agent, said conjugating agent corresponding to the formula (I):

$$Q\text{---}(S\text{---}PO_3^{-2})_n \qquad (I)$$

wherein n is at least 1 and Q is a straight or branched monomer, polymer or oligomer having an average molecular weight between about 200 and about 1,000,000 and wherein when n is 1, Q comprises at least 1 additional reactive functionality, and (b) contacting said conjugating agent (I) with at least two compounds, wherein at least one of said compounds is functionalized with an electrophilic group and at least two of said compounds are bound to said conjugating agent.

2. The method of claim 1 wherein n is an integer between 2 and 50.

3. The method of claim 1 wherein said compound (I) is selected from the group consisting of: carboxymethylamylose poly(phosphorothioate), poly(acrylamide) poly[acryloyl(2-(2-phosphorothioethyl)aminoethyl] hydrazide, poly(glutamic acid) poly(phosphorothioate), poly(styrene) poly(phosphorothioate), poly(acrylamide) poly(phosphorothioate), dextran poly(phosphorothioate), N-hydroxysuccinimidyl cysteamidophosphorothioate 4,5-dithioheptyl 1-carboxylate, N-hydroxysuccinimidyl cysteamidophosphorothioate 3-oxybutyl 1-carboxylate, N-hydroxysuccinimidyl cysteamidophosphorothioate heptanoyl 1-carboxylate, cysteamidophosphorothioate heptanoyl 1-hydrazide, cysteamidophosphorothioate heptanoyl 1-(aminoethyl)carboxamide, and p-nitrophenyl cysteamidophosphorothioate heptanoyl 1-carboxylate.

4. The method of claim 1 wherein activating said compound corresponding to the formula (I) comprises contacting said compound with a hydrogen ion concentration between about pH 4.0 and about 5.5 or a phophatase enzyme.

5. The method of claim 6 wherein said compound that displays an electrophilic group is selected from the group consisting of: detectable moieties, solid phases, binding members, and combinations thereof.

6. A method of crosslinking compounds comprising the steps of:

(a) activating a compound by deprotecting a thiol group of a phosphothorothioate monoester of said compound, said compound corresponding to the formula (I):

$$Q\text{---}(S\text{---}PO_3^{-2})_n \qquad (I)$$

wherein n is at least 1 and Q is a straight or branched monomer, polymer or oligomer having an average molecular weight between about 200 and about 1,000,000 and wherein when n is 1, Q comprises at least 1 additional reactive functionality, and (b) contacting said activated compound (I) with at least one compound that is functionalized with at least one electrophilic group and a second group capable of reaction with said activated compound or at least two compounds that are functionalized with at least one electrophilic group, said electrophilic groups selected from the group consisting of heterobifunctional linkers, haloacetyl groups, acrylate groups, quinone groups, epoxide groups, thiopyridyl groups, and transition metal complexes or transition metals in various oxidation states or in colloidal forms, whereby crosslinking is effected creating stabilization of said crosslinked compound.

7. The method of claim 6 wherein n is an integer between 2 and 50.

8. The method of claim 6 wherein said compound (I) is selected from the group consisting of:carboxymethylamylose poly(phosphorothioate), poly(acrylamide) poly[acryloyl(2-(2-phosphorothioethyl)aminoethyl]hydrazide, poly(glutamic acid) poly(phosphorothioate), poly(styrene) poly(phosphorothioate), poly(acrylamide) poly(phosphorothioate), dextran poly(phosphorothioate), N-hydroxysuccinimydyl cysteamidophosphorothioate 3-oxybutyl 1-carboxylate, N-hydroxysuccinimydyl cysteamidophosphorothioate heptanoyl 1-carboxylate, cysteamidophosphorothioate heptanoyl 1-hydrazide, cysteamidophosphorothioate heptanoyl 1-(aminoethyl)carboxamide, and p-nitrophenyl cysteamidophosphorothioate heptanoyl 1-carboxylate.

9. The method of claim 6 wherein activating said compound corresponding to the formula (I) comprises contacting said compound with a hydrogen ion concentration between about pH 4.0 and about 5.5 or a phosphatase enzyme.

10. The method of claim 6 wherein said compound that displays an electrophilic group is selected from the group consisting of: detectable moieties, solid phases, binding members, and combinations thereof.

* * * * *

UNITED STATES PATENT AND TRADEMARK OFFICE
CERTIFICATE OF CORRECTION

PATENT NO. : 5,789,219
DATED : August 4, 1998
INVENTOR(S) : Bieniarz et al.

It is certified that error appears in the above-identified patent and that said Letters Patent is hereby corrected as shown below:

On the title page item [54]
Column 1, line 2, change "crosslinking" to --crosslinking,--.

Column 16, line 25, change "mglml" to --mg/ml--.

Column 18, line 61, change "ugmol" to --µmol--.

Column 19, line 61, change "ugmol" to --µmol--.

Column 20, line 3, change " A566 " to -- $A_{566}$ --.

UNITED STATES PATENT AND TRADEMARK OFFICE
CERTIFICATE OF CORRECTION

PATENT NO. : 5,789,219
DATED : August 4, 1998
INVENTOR(S) : Bieniarz et al.

It is certified that error appears in the above-identified patent and that said Letters Patent is hereby corrected as shown below:

Column 26, line 66, change "ugmol" to --µmol--.

Column 27, line 4, change "overnight" to --overnight.--. (1st. occurr.)

Column 29, line 17, change "20 (b)" to --(b)--.

Signed and Sealed this

Second Day of March, 1999

Attest:

Q. TODD DICKINSON

*Attesting Officer*   Acting Commissioner of Patents and Trademarks